(12) United States Patent
Greif et al.

(10) Patent No.: US 7,691,987 B2
(45) Date of Patent: Apr. 6, 2010

(54) USE OF A NOVEL EIMERIA GENE AND CORRESPONDING PROTEIN

(75) Inventors: Gisela Greif, Remagen (DE); Ralf Hosse, Düsseldorf (DE); Jürgen Krücken, Korschenbroich (DE); Frank Wunderlich, Neuss (DE)

(73) Assignee: Bayer Animal Health GmbH (DE)

( * ) Notice: Subject to any disclaimer, the term of this patent is extended or adjusted under 35 U.S.C. 154(b) by 422 days.

(21) Appl. No.: 10/562,324

(22) PCT Filed: Jun. 30, 2004

(86) PCT No.: PCT/EP2004/007080

§ 371 (c)(1),
(2), (4) Date: Jun. 29, 2006

(87) PCT Pub. No.: WO2005/005422

PCT Pub. Date: Jan. 20, 2005

(65) Prior Publication Data

US 2007/0184054 A1     Aug. 9, 2007

(30) Foreign Application Priority Data

Jul. 4, 2003  (DE) ............................... 103 30 235

(51) Int. Cl.
C07H 21/04 (2006.01)
C07H 21/02 (2006.01)
C12N 15/63 (2006.01)
C12N 15/85 (2006.01)
C12N 15/86 (2006.01)
C12N 1/20 (2006.01)
C12N 15/00 (2006.01)
C12Q 1/68 (2006.01)

(52) U.S. Cl. ................... 536/23.1; 435/320.1; 435/325; 435/252.1; 435/69.1; 435/6

(58) Field of Classification Search ................ None
See application file for complete search history.

(56) References Cited

U.S. PATENT DOCUMENTS 5,187,080 A * 2/1993 Andrews et al. ........... 435/69.3

OTHER PUBLICATIONS

Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp: 8-9, 2002.*

* cited by examiner

*Primary Examiner*—Delia M Ramirez
*Assistant Examiner*—Jae W Lee

(74) *Attorney, Agent, or Firm*—Jessica Monachello

(57) ABSTRACT

The invention relates to a novel oocyst sporocyst protein (EtOs22) belonging to the parasite of the species *Eimeria tenella* and to the polynucleotide encoding this protein, to vectors which contain this polynucleotide, to cells which are transformed with these vectors, to antibodies which are directed against the protein, to vaccines which comprise the polynucleotide, the protein, or fragments thereof, the above-mentioned vectors or antibodies directed against the protein, and to the use of polynucleotide or of polypeptide for finding active compounds for treating an infection with *Eimeria* and active compounds which are suitable for the therapy of an infection with *Eimeria*.

6 Claims, 5 Drawing Sheets

Fig.1

```
  1  caggacccca aaataaaatc aaaggctatc acactatttt acttcttaac cgtttactga
             SEQ ID. NO. 6
 61  ggctacaaga acaagtttga agatgaggac tatcctagcc accctagtcg gtttcacagc
  1                             M  R  T  I  L  A  T  L  V  G  F  T 121  ctgcgcagcc gttgctgcag acggagcacc tgagtatcct tctcagcttg cagttgaaat
 13   A  C  A  A  V  A  A  D  G  A  P  E  Y  P  S  Q  L  A  V  E 181  cgatccagaa gcgattattg cgatccagca agatgcaaac gccgacccac gtctcttttt
 33   I  D  P  E  A  I  I  A  I  Q  Q  D  A  N  A  D  P  R  L  F 241  cccactgagc gggcttgtct ccgccaaact tgccaaagtc tttcaaccca acatataccc
 53   P  L  S  G  L  V  S  A  K  L  A  K  V  F  Q  P  N  I  Y 301  aacccctcct agtccccaga caacttacca ctttcacctc catcctcatc cccattatcc
 73   P  T  P  P  S  P  Q  T  T  Y  H  F  H  L  H  P  H  P  H  Y 361  gcatcctcag ccaagttatc ctcat
 93   P  H  P  Q  P  S  Y  P  H  P  Q  P  H  H  P  H  P  H  P  Y 421
113   H  P  H  P  H  P  H  H  P  H  P  H  Q  H  P  H  R  H 481                                                        g ttcatgtgcc
133   P  D  H  H  P  H  H  H  P  H  H  H  H  E  H  N  V  H  V 541  tcaacatcag cacgctcaac acaacggcca ccagaacaac ggtggcccag ctcattatca
153   P  Q  H  Q  H  A  Q  H  N  G  H  Q  N  N  G  G  P  A  H  Y 601  ccatgactac cattttgcgc atcctcatca agagaaccag catcaccgcg aggaagagca
173   H  H  D  Y  H  F  A  H  P  H  Q  E  N  Q  H  H  R  E  E  E 661  gcttaccgac atcaactaag ctattggtcg ggaattaagg tgcttagtct cagtagtcag
193   Q  L  T  D  I  N  -
```

Fig. 1 cont.

```
 721  tacagtacta ggctacgtct gagatcttca tggcaaagag gtaccagcca ccaagctgac
 781  tcggctatgt tttattagac aaatttaaat ttaaagggtc ccagtttcag tctctgcagg
 841  tctgcccctg aaagcacgag aggggcctaa agggtgattg gagctgcaaa tacagctgca
 901  aatgcagctg caaagtgccg cttcaaaaaa gggacaggct tcccgccaaa attttggat
 961  catacctatc aatgcttcga gaaaacatag aaaacaaaag cactgaagaa cgttcatagt
1021  cggtagtttt aggggcatgc cgtgtgctaa aatcccatcg aaccttcagg tacacctgat
1081  cgttacgaag tacacaccac cggtcactct caacgcgcac cactagagcg agagctgctt
1141  cagggatgca gcgagatgtc gactcagagg tcctacatta aaggg(a)ₙ
```

− 1,1 kb

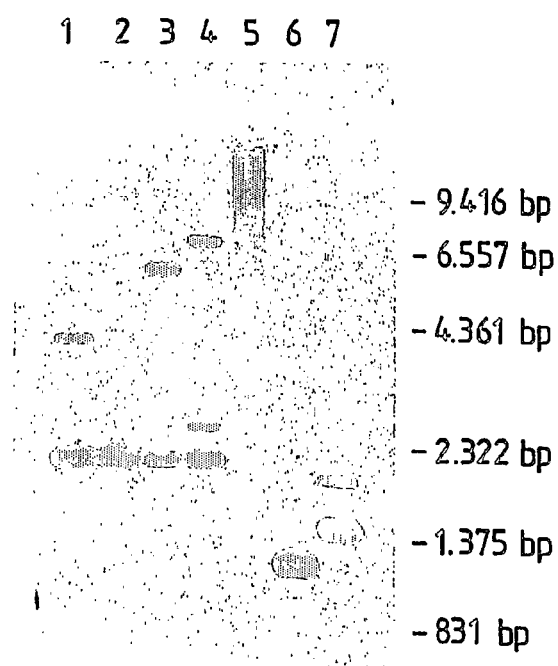
Fig. 4
1 2 3 4 5 6 7
- 9.416 bp
- 6.557 bp
- 4.361 bp
- 2.322 bp
- 1.375 bp
- 831 bp
Fig. 5
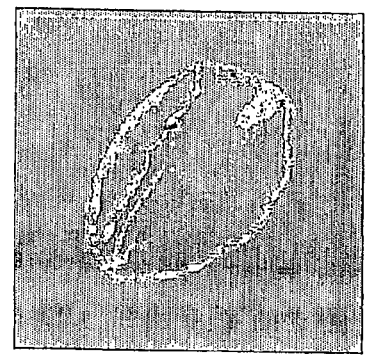
5.1
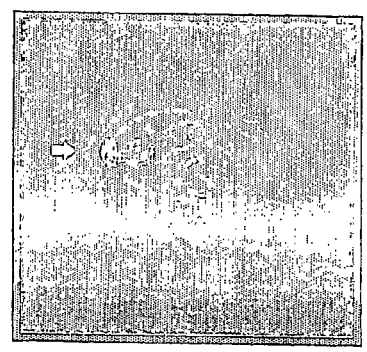
5.2
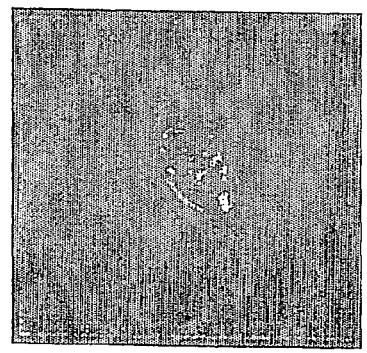
5.3

USE OF A NOVEL EIMERIA GENE AND CORRESPONDING PROTEIN

The invention relates to a novel oocyst sporocyst protein (EtOS22) belonging to the parasite of the species *Eimeria tenella* and to the polynucleotide encoding this protein, to vectors which contain this polynucleotide, to cells which are transformed with these vectors, to antibodies which are directed against the protein, to vaccines which comprise the polynucleotide, the protein, or fragments thereof, the above-mentioned vectors or antibodies directed against the protein, and to the use of polynucleotide or of polypeptide for finding active compounds for treating an infection with *Eimeria* and active co mounds which are suitable for the therapy of an infection with *Eimeria*.

PRIOR ART

Parasites of the genus *Eimeria* are obligatorily intracellular protozoa which have a complicated lifecycle which gives rise sequentially to sexual and asexual developmental stages. *Eimeria tenella* lives in the cecum of the domestic hen (*Gallus domesticus*) and is closely related to the human pathogens *Toxoplasma gondii*, *Plasmodium falciparum* and *Cryptosporidium parvum*, and to the genera *Sarcocystis*, *Neospora*, *Babesia* and *Theileria*, which are important animal pathogens. According to the systematic classification of the protozoa by LEVINE (1980), representatives of these genera belong to the Apicomplexa phylum.

*Eimeria tenella* is the causative agent of poultry coccidiosis, a disease which has become an economically important problem in conjunction with the intensive floor management of chicks and hens. The pathology of a coccidial disease includes bloody diarrheas, which can cause serious economic damage as a result of the hens decreasing their feed intake and losing weight. Aside from *Eimeria tenella*, six other *Eimeria* species are responsible for coccidial disease in the domestic hen: *Eimeria acervulina*, *Eimeria maxima*, *Eimeria brunetti*, *Eimeria necatrix* and *Eimeria praecox*.

The infectious forms of apicomplex parasites (sporozoites and merozoites) are characterized by special morphological properties which distinguish them unambiguously from other sporozoa. The most important feature is regarded as being an "apical complex" at the anterior cell pole, which complex is composed of three secretory organells (rhoptries, micronemes and dense granules) and also the structure-forming conoid possessing polar rings and subpellicular microtubules.

*Eimeria tenella* passes through a monoxene development in the domestic hen (*Gallus gallus*). The parasite is strictly host-specific and obligatorily intracellular. Propagation takes place in epithelial cells-and in the submucosa of the cecum. The domestic hen becomes infected with *Eimeria tenella* when seeking food. After sporulated oocysts have been ingested and mechanically processed in the gizzard, mature, resting sporozoites are released from the sporocysts, at what is termed the Stieda body, in the small intestine under the influence of trypsin and bile salts. The sporozoites become mobile and colonize host cells in the cecum while forming a parasitophorous vacuole. The parasitophorous vacuole protects the intracellular parasite from lysosomal digestion. Within its protection, multinuclear schizonts are formed. Schizogony (merogony) constitutes an asexual reproduction of the parasite. Mobile merozoites pinch themselves out of the schizont in the form of a rosette. After they have been released, the merozoites establish up to 3 further generations of schizonts in adjacent cecal cells. During an acute infection, the cycles of schizogony give rise to extensive intestinal lesions which can lead to intestinal hemorrhages, weight loss and, in the case of a severe infection, to the death of the host. After the cycles of schizogony have come to an end, gamogony begins, with the formation of multinuclear male microgamonts and mononuclear female macrogamonts, which mature into gametes. The macrogamete contains eosinophilic "all-forming" bodies which, after fertilization, fuse and build the oocyst wall. After the prepatency time of 6 days has come to an end, new oocysts are secreted. With the secretion of the oocysts, the infection has come to an end and the host has acquired species-specific immunity.

Diagnosis

The ability to identify the coccidial species in hens accurately, rapidly and inexpensively is of the greatest possible importance for the prophylaxis and treatment of an infection. The method of Long and Reid 1982 is currently used routinely to identify the seven *Eimeria* species in the hen in accordance with oocyst morphology (microscopic), host specificity, the pathology of the lesions in the intestine and the prepatency time. In addition to this, there is also the attempt to effect a biochemical characterization by way of isoenzyme patterns. In this method, enzymes of sugar metabolism are for the, most part used as genetic markers for constructing a zymogram (Johnston and Fernando 1997). Experience has shown that accurate species differentiation can only be inadequately or partly achieved when using either the conventional, morphologically descriptive procedure or the biochemical methods. It is therefore desirable to be able to characterize species at the recombinant DNA level. Only very few conflicting investigative results have thus far been obtained in this field (Comes et al. 1996). The biological diversity of *Eimeria* species suggests that genetic differences in the form of DNA-polymorphisms exist in the different species. Polymorphisms can arise as a result of base changes (deletion, insertion) or as a result of chromosomal rearrangements. In the DNA finger printing method, which was developed originally for relatedness analysis, the variable DNA is cut with restriction endonucleases, hybridized with radioactive DNA probes and, after gel electrophoresis and Southern blotting, visualized in autoradiography. The genetic finger print which has been produced in this way can be used to unambiguously differentiate the species and strain of organisms. The RAPD-PCR method "random amplified polymorphic DNA polymerase chain reaction" offers a simplification of this approach. The method is based on amplifying genomic DNA in a polymerase chain reaction (PCR) using single primers which have a random nucleotide sequence. After having been separated on an agarose gel and stained with ethidium bromide, amplified DNA segments (RAPD-PCR markers) give rise to a specific band pattern. However, this method can only be used to distinguish pure strains from each other. It is not possible to use these techniques to identify a species in a field isolate (mixture of different *Eimeria* species). A technically simpler and therefore more economic method would be to find a specific probe which is based on a specific gene sequence. Thus far, only known sequences of ribosomal DNA (Ellis and Bumstead 1990) from the internal transcriber spacer ITS1 (Schnitzler et al. 1998) and ITS2 (Gasser et al. 2001) regions, as well as an *Eimeria acervulina* sporozoite antigen (EASZ 240/160) (Molloy et al. 1998), have been used for this purpose.

Therapy

Anticoccidials to an annual value of at least 300 million U.S. $ are currently being used for the therapy of this disease. Since 1970, chemotherapeutic treatment has, in particular, been carried out using the polyether ionophores monensin, narasin, salinomycin and lasalocid. In addition, a large number of active compounds which inhibit the DNA synthesis or the protein synthesis of the parasite stages are also on the market (Greif 2001). However, the present therapies suffer from serious problems and/or disadvantages. Aside from the serious drug burden in the hen (residue problems in edible tissues) and the ecotoxicological/ecobiological pollution (of the environment), the development of drug resistance is regarded as being the greatest problem involved in treating with anticoccidials. Attempts are made to combat the resistances which develop by using what are termed shuttle or rotation programs and by expensively searching for novel mechanisms of action (Coombs 2002). There is therefore an urgent need for improved active compounds for treating *Eimeria* infections and for methods for finding these active compounds.

Vaccination

Immunoprophylaxis (vaccination) would be a far better alternative to treating coccidiosis chemotherapeutically. One pathogen contact with *Eimeria* species leads to virtually complete immunity against a second homologous infection (Rose and Wakelin 1990). In one-day-old chicks, the continuous administration of parasite stages over a period of 16-25 days induces natural immunity to *Eimeria tenella, Eimeria acervulina* and *Eimeria maxima* (Stiff and Bafundo 1993). Immunizing laying hens with protective gametocyte antigens improves the immunity situation in hatched chicks. This strategy was developed by Wallach as "maternal immunization" (Wallach 1992).

Vaccine programs employing fully virulent *Eimeria* strains (oocyst live vaccines) are currently being carried out using the commercial products Immucox® (Vetech Laboratories, Canada) and Coccivac® (Sterwin Laboratories; USA). The products Paracox® (Schering Plough, England) and Livacox® (Williams 2002) are based on what are termed attenuated virulent strains. Polyether-resistant virulent live vaccines have also recently come onto the market (Vermeulen 2001). In all, 13 oocyst-containing live vaccines are currently. registered for immunizing against coccidiosis in hens (Chapman et al. 2002, Williams 2002).

However, all these vaccines which are on the market suffer from the economic disadvantage of high production costs and the livestock management which is required for the passage of the oocysts. An additional problem is that the live vaccines which are on the market could mutate back to the original pathogenic type.

There is therefore an urgent need to make available. improved vaccines which are preferably not live vaccines.

The development, by genetic manipulation, of a recombinant vaccine (a subunit vaccine) which is based on what are termed protective antigens is regarded as being the "ideal goal" of all immunization methods. Protective antigens are structural compounds in the parasite which, during the parasite/host cell interaction, have an important function in cell recognition, cell adhesion and cell invasion and also, possibly, other proteins whose function has not hitherto been known. Previous searching for protective *Eimeria tenella* antigens has encompassed surface antigens and inner organell antigens, and also gradient-isolated organell antigens, of oocysts, sporozoites and merozoites (Vermeulen 1998). Apart from deliberately searching for gene sequences for proteins which are already known, random searching in EST (expressed sequence tags) databases (Wang et al. 1999) or phage display libraries (Silva, A. et al. 2002) is also used for finding new genes and targets. Danforth et al. (1985) were the first to prepare an *Eimeria tenella* antigen, of 60-70 kDa, in vitro on the basis of recombinant DNA techniques. Since this experiment, a few selective *Eimeria tenella* oocyst antigens (Clark 1986, Crane et al. 1991, Bhogal et al. 1992, Eschenbacher et al. 1996), *Eimeria tenella* sporozoite antigens (Files et al. 1987, Miller et al. 1989) and *Eimeria tenella* merozoite antigens (Ko et al. 1990, Binger et al. 1993) have been prepared recombinantly. Crane et al. (1991) used a recombinant *Eimeria tenella* antigen to induce crossreactive protection against four *Eimeria* species in the hen. However, despite many attempts at immunization using recombinant antigens, no satisfactory results have thus far been achieved, which means that there is a great need for identifying novel, previously unknown antigens and their appurtenant gene sequences (Jenkins 1998, Vermeulen 2001).

DESCRIPTION OF THE FIGURES

FIG. 1 shows the DNA sequence, and the deduced amino acid sequence, in the case of the EtOS22-cDNA. The primers A17-f-length-64-up and A17-f-length-1176-low are underlined. The signal peptide is underlaid in pale gray. The original sequence of the clone which was enriched in the phase panning, and which was used for carrying out the 5'- and 3'-RACE-PCR, is underlayed in dark gray.

FIG. 4 shows a genomic Southern blot for EtOS22. 10 µg of genomic *E. tenella* DNA were separated gel-electrophoretically, and blotted, in each lane. This DNA had previously been digested with the following restriction endonucleases: BglI (1), ClaI (2), KpnI (3), AccI (4), BglII (5), DraI (6) and MvaI (7). The blot was hybridized with the radioactively labeled PCR product from position 1 to position 1106 (1106 bp).

FIGS. 5.1-5.3 show immunofluorescence against EtOS22 in *E. tenella*. The Mab $E_2E_5$ (mouse IgG2a) was used as the primary antibody while a goat anti-mouse IgG conjugate, Alexa 488, was used as the secondary antibody. The figures show an empty oocyst shell (5.1), a ruptured sporocyst (5.2) an intact sporocyst (5.3). The region of the Stieda body is marked with an arrow.

DESCRIPTION OF THE INVENTION

Figure 2:
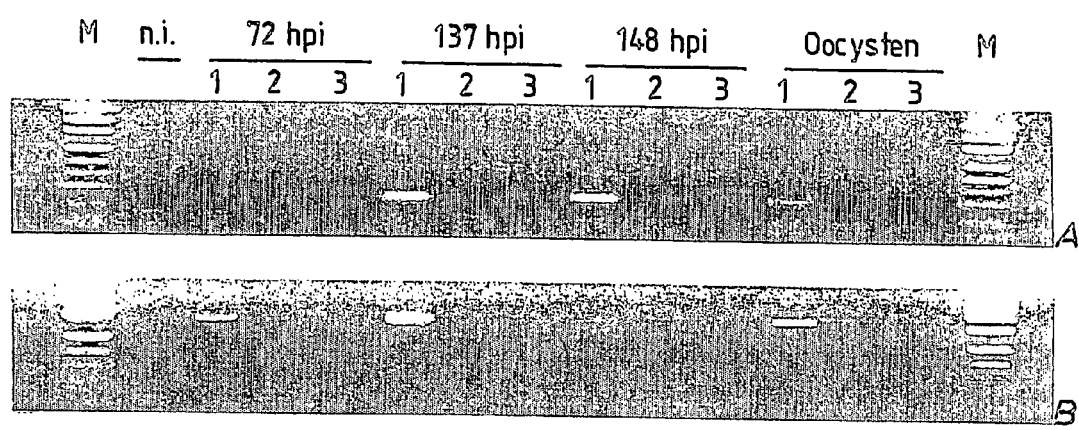
FIG. 2 shows the use of RT-PCR to determine the expression pattern of EtOS22. In each case 1 µg of pUC-Mix markers (MBI Fermentas, St. Leon-Rot) was used as the DNA length standard (M). cDNA from uninfected chick ceca (ui,), as well as from infected chick ceca 72, 137 and 148 h after infection (72 hpi, 137 hpi and 148 hpi), and from sporulated oocysts, was used as templates for the PCR reactions. The PCR products which were amplified using the primers A17-22-up and A17-112-low are of 91 bp in size (A), while the PCR products which were amplified using the primers EtAC-TIN-up and EtACTIN-low are of 350 bp in size (B). Reaction mixtures containing reverse transcriptase MT) and containing RNA template were in each case loaded in the lanes marked (1), while reaction mixtures without RT but containing RNA template were in each case loaded in the lanes marked (2) and reaction mixtures containing RT but not containing any RNA template were in each case loaded in the lanes marked (3).

The invention relates to a novel oocyst sporocyst protein (EtOS22) from the parasite of the species *Eimeria tenella*.

The invention also relates to the polynucleotide which encodes this protein. SEQ ID NO:1 shows the full-length mRNA which contains the DNA sequence which encodes the novel *Eimeria tenella* oocyst sporocyst protein. The open reading frame (ORF) which encodes the protein (SEQ ID NO:2) is shown in SEQ ID NO:3.

In addition, the invention is based on the discovery that the novel protein EtOS22 from the parasite of the species *Eimeria tenella* is involved in the excystation of the sporozoites from the sporocysts and is consequently essential for the lifecycle of the parasite. The excystation can be inhibited by antibodies directed against EtOS22.

EtOS22 is an intronless gene which consists of a single coding exon. The EtOS22 gene ORF, which is of 594 bp in size, is present in two copies in the genome clone 2257242.c007101021.Contigl (71.864 bp, status: 03.03.2003). However, EtOS22 probably occurs in substantially more than 2 copies in the *Eimeria tenella* genome.

The invention also relates to:
a) a polynucleotide which exhibits an identity of more than 50%, 60%, 70% or 80%, preferably more than 85% or 90%, and particularly preferably more than 95% or 97%, with the polynucleotide having the sequence depicted in SEQ ID NO:1 or 3;
b) a polynucleotide which hybridizes, under stringent conditions, with the polynucleotide having the sequence depicted in SEQ ID NO:1 or 3;
c) a polynucleotide which exhibits an identity of more than 50%, 60%, 70% or 80%, preferably more than 85% or 90%, and particularly preferably more than 95% or 97%, with a polynucleotide which encodes the polypeptide having the sequence depicted in SEQ ID NO:2;
d) a polynucleotide which hybridizes, under stringent conditions, with a polynucleotide which encodes the polypeptide having the sequence depicted in SEQ ID NO:2;
e) a polynucleotide which differs from the polynucleotide depicted in SEQ ID NO:1 due to the degeneracy of the genetic code; and
f) a polynucleotide which is a fragment of a polynucleotide as described in a) to e) and is at least 6 nucleotides or 8 nucleotides in length, preferably more than 10 or 20 nucleotides in length, particularly preferably more than 50 or 100 nucleotides in length and, very particularly preferably, more than 200 or more than 500 nucleotides in length.

A polynucleotide having the sequence SEQ ID NO:1 or 3, and also the abovementioned polynucleotides a) to f), are termed EtOS22 polynucleotides in that which follows.

The invention furthermore relates to a polypeptide which is encoded by a nucleic acid as described in a) to f) and is at least 8 amino acids in length. This polypeptide, and the polypeptide depicted in SEQ ID NO:2, are termed EtOS22 polypeptides in that which follows.

The invention also relates to an expression system or vector which contains at least one of the polynucleotides as described in a) to f) and an expression control sequence. The expression system enables the EtOS22 polypeptide according to the invention to be expressed.

In this connection, the expression of EtOS22 is preferably under the control of the cytomegalovirus (CMV) promoter. A BGH (bovine growth hormone) polyadenylation signal in turn terminates the transcription and is responsible for polyadenylating the mRNA.

Examples of particularly preferred expression control sequences are the early or late SV40 or adenovirus promoter, the lac system, the trp system, the TAC system, the TRC system, the main operator and promoter regions of phage λ, the control regions of the fd envelope protein, the 3-phosphoglycerate kinase promoter, the acid phosphatase promoter and the yeast α-mating factor promoter.

The invention also relates to a host cell which harbors the above-described vector or the expression system.

Preferred examples of the host cell are: *E. coli, Pseudomonas, Bacillus, Streptomyces*, yeast cells, CHO cells, R1.1 cells, B-W cells, L-M cells, COS 1 cells, COS 7 cells, BSC1 cells, BSC40 cells and BMT10 cells, plant cells, insect cells and mammalian cells in cell culture. Expression in a eukaryotic system is effected particularly preferably in the baculovirus system, particularly in a system which permits the introduction of posttranslational modifications.

The invention also relates to fusion proteins which comprise an EtOS22 polypeptide as described above. In this connection, the fusion protein can contain another polypeptide moiety which is relevant for an additional activity of the fusion protein [e.g. β-galactosidase, β-glucuronidase, green fluorescent protein (GFP), autofluorescent proteins, such as blue fluorescent protein (BFP), glutathione S transferase (GST), luciferase, horseradish peroxidase (HRP) and chloramphenicol acetyl transferase (CAT)]. In addition, or as an alternative, epitope tags can form part of the fusion protein [e.g. His tags, FLAG tags, influenza hemagglutinin (HA) tags, Myc tags, VSV-G tags or thioredoxin (Trx) tags]. Fusion proteins can also contain maltose-binding protein (MBP), S tags, Lex DNA-binding domains, GAL4 DNA-binding domains or herpes simplex virus (HSV) BP16 protein.

The invention also relates to a method for preparing an EtOS22 polypeptide or a fusion protein, as described above, in appropriate prokaryotic or eukaryotic. expression systems. In this connection, the expression can be effected permanently or transiently in a cell line which is in each case appropriate, or in appropriate host cells, as described above. The known host/vector systems such as bacteria (e.g. *Streptomyces* spp., *Bacillus subtilis, Salmonella typhimurium, Serratia marcescens* and, in particular, *Escherichia coli*) are suitable prokaryotic expression systems.

This invention also relates to the use of EtOS22 polynucleotides for detecting polynucleotides from parasites of the genus *Eimeria*, preferably *Eimeria acervulina Eimeria maxima, Eimeria brunetti, Eimeria necatrix, Eimeria praecox* and, particularly preferably, *Eimeria tenella*. In this connection, the invention relates. to polynucleotides which are able to hybridize with polynucleotides from the abovementioned parasites. The invention relates, in particular, to the use of these polynucleotides as:
a) probes in Northern or Southern blot assays,
b) polynucleotides or oligonucleotides which are bound on microarrays or macroarrays,
c) primers for PCR or analogous methods which are used for diagnosing the abovementioned parasites, with the DNA of the parasites in question being specifically identified, and amplified, using the primers and the PCR technique.

This invention also relates to antibodies which react specifically with an epitope of an EtOS22 polypeptide.

This invention also relates, in particular, to monoclonal antibodies which react specifically with an epitope of an EtOS22 polypeptide.

This invention also relates to the use of the abovementioned antibodies as parasiticides. Antibodies are preferably used for treating *Eimeria* infections and particularly preferably for treating *Eimeria tenella* infections. The abovementioned antibodies are preferably used for treating infections of poultry and particularly preferably used for treating infections of chickens.

Diagnosis

This invention furthermore relates to the use of EtOS22 polynucleotides, or of the abovementioned antibodies directed, against EtOS22 polypeptides, for diagnosing *Eimeria* infections and, preferably, *Eimeria tenella* infections.

The invention also relates to a kit which comprises EtOS22 polynucleotides, or antibodies directed against EtOS22 polypeptides, and instructions for implementing the diagnostic method.

Vaccines

The invention also relates to a method for preparing an immunogenic composition for immunizing poultry, and preferably chickens, which composition comprises at least one of the abovementioned EtOS22 polypeptides according to the invention or at least one of the abovementioned antibodies.

The invention also relates to the use of the above-described expression vectors, containing one of the abovementioned EtOS22 polynucleotides, for preparing an immunogenic composition which is to be administered in a host for the purpose of activating a protective immune response in this host, which immune response is directed towards the *Eimeria* EtOS22-homologous protein or towards the *Eimeria tenella* EtOS22 protein.

This invention also relates to the use of the abovementioned EtOS22 polypeptides for preparing vaccines against coccidiosis.

The invention also relates to:
1. an inactivated vaccine comprising
   a) at least one of the abovementioned EtOS22 polypeptides which
      i. is isolated from the parasite stages, or
      ii. is prepared synthetically in vitro, or
      iii. is prepared using recombinant DNA technology; or
   b) a fusion protein, as mentioned above, which comprises one of the abovementioned EtOS22 polypeptides, with it being possible for the polypeptide or fusion protein to have been modified in vivo or in vitro by means of amidation, carboxylation or phosphorylation.
2. A vector vaccine comprising:
   a) a self-replicating vector (e.g. bacteria, fungi or viruses) which contains one of the above-described EtOS22 polynucleotides which preferably gives rise to the long-term synthesis of an EtOS22 polypeptide and to antigen presentation, resulting in the immune system being stimulated; or
   b) a plasmid which contains an EtOS22 polynucleotide; or
   c) a pure EtOS22 polynucleotide (naked-DNA);
3. A passive vaccine comprising:
   a) antibodies which are directed against immunogenic epitopes of the EtOS22 polypeptide; or
   b) antiidiotypic antibodies, i.e. antibodies which are directed against the idiotype of the antibodies which bind to an EtOS22 polypeptide.

Screening Methods

This invention also relates to a method for identifying active compounds, such as small organic molecules, peptides or antibodies, which modulate the function of the EtOS22 polypeptide as depicted in SEQ ID NO:2 and thereby modulate the excystation of the sporozoites from the *Eimeria* sporocysts. The degree of the modulation is at least 10%, preferably at least 20%, particularly preferably at least 30% and very particularly preferably at least 50%.

The invention also relates to a method for finding active compounds which modulate the activity of the EtOS22 protein in connection with the excystation of sporozoites from sporocysts, in which method:
a) the active compound to be tested is brought into contact with an EtOS22 polypeptide as claimed in claim 2, with the selected conditions enabling the test substance to bind specifically to the EtOS22 polypeptide; and
b) a specific binding to the polypeptide which has taken place is detected;

with an active compound which binds to the polypeptide being identified as a potential active compound for treating the coccidiosis.

The invention also relates to a method for finding active compounds which modulate the activity of the EtOS22 protein in connection with the excystation of sporozoites from sporocysts, in which method:
a) the active compound to be tested is brought into contact with an EtOS22 polypeptide as claimed in claim 2, with the selected conditions enabling the test substance to bind specifically to the EtOS22 polypeptide; and
b) a modulation of the activity of the polypeptide as claimed in claim 2, or of the EtOS22 protein, is detected;

with an active compound which modulates the activity being identified as a potential active compound for treating coccidiosis.

The invention also relates to a method for finding active compounds for treating coccidiosis, in: which method the EtOS22 protein is used, in its recombinant form, for screening libraries of chemical compounds based on affinity selection and mass spectrometry. For the purpose of finding inhibitors for the target protein, which has a function which is unknown but which is essential for the survival of the sporozoite, it is possible to use screening methods which test substance libraries with regard to affinity for the protein. One screening possibility is that of affinity selection from substance mixtures, with the ligands subsequently being detected in the mass spectrometer. For this, it is necessary to use defined substance mixtures from which individual substances can be identified with the. aid of the mass detection. For this reason, substance mixtures which have been prepared from combinatorial syntheses are particularly suitable for this screening method.

Substances which are conspicuous in the affinity selection are subjected to further tests such as the *Eimeria tenella* in-vitro test.

The invention also relates to novel active compounds which are identified using the above-described methods and which are suitable for modulating the excystation of the sporozoites from the *Eimeria* sporocysts. The novel active compounds modulate the excystation by at least 10%, preferably by at least 20%, particularly preferably by at least 30% and very particularly preferably by at least 50%.

The invention also relates to novel active compounds which modulate the excystation of the sporozoites from the *Eimeria* sporocysts. The novel active compounds modulate the excystation by at least 10%, preferably by at least 20%, particularly preferably by at least 30% and very particularly preferably by at least 50%.

The invention also relates to the use of novel active compounds, which have been identified using one of the above-described methods, for producing a drug for the prophylactic or therapeutic treatment of poultry and, preferably, chickens which may be infected, or have been infected, with *Eimeria*. The drugs according to the invention comprise at least one of the active compounds identified using one of the above-described methods and can be administered nasally, dermally, parenterally or enterally.

The invention also relates to the use of novel active compounds, which modulate the excystation of the sporozoites from the *Eimeria* sporocysts by at least 10%, preferably by at least 20%, particularly preferably by at least 30% and very particularly preferably by at least 50%, for producing a drug for the prophylactic or therapeutic treatment of coccidiosis. Preference is given to using the active compounds for producing a drug for treating poultry and, particularly preferably chickens, which may be infected, or have been infected, with *Eimeria*. The drugs according to the invention comprise at least one of the active compounds which have been identified using the above-described methods and can be administered nasally, dermally, parenterally or enterally.

Pharmaceutical Compositions

The active compounds can be used both prophylactically and therapeutically.

The active compounds are used enterally, parenterally, dermally or nasally either directly or in the form of suitable preparations.

The active compounds are used enterally, for example orally, in the form of powders, suppositories, tablets, capsules, pastes, drinks, granules, drenches, boli, medicated feed or drinking water. They are used dermally, for example, in the form of dipping, spraying, bathing, washing, pouring-on and spotting-on and powdering. They are used parenterally, for example, in the form of injection (intramuscular, subcutaneous, intravenous or intraperitoneal) or by means of implants.

Suitable preparations are: solutions, such as injection solutions, oral solutions, concentrates for oral administration following dilution, solutions for use on the skin or in body cavities, pour-on formulations, gels; emulsions and suspensions for oral or dermal use and also for injection; semisolid preparations; formulations in which the active compound is worked into an ointment base or into an oil in water or water in oil emulsion base; solid preparations, such as powders, premixes or concentrates, granules, pellets, tablets, boli and capsules; aerosols and inhalates, and active compound-containing molded bodies.

Injection solutions are administered intravenously, intramuscularly and subcutaneously. Injection solutions are produced by dissolving the active compound in a suitable solvent and, where appropriate, adding additives such as solubilizers, acids, bases, buffer salts, antioxidants and preservatives. The solutions are sterilized by filtration and bottled.

Solvents which may be mentioned are: physiologically tolerated solvents such as water, alcohols, such as ethanol, butanol, benzyl alcohol and glycerol, hydrocarbons, propylene glycol, polyethylene glycols and N-methylpyrrolidone, and also mixtures thereof.

The active compounds can also be dissolved, where appropriate, in physiologically tolerated vegetable or synthetic oils which ate suitable for injection. Solubilizers which may be mentioned are: solvents which promote the dissolution of the active compound in the main solvent or prevent it from precipitating out. Examples are polyvinylpyrrolidone, polyethoxylated castor oil and polyethoxylated sorbitan esters.

Preservatives are: benzyl alcohol, trichlorobutanol, p-hydroxybenzoic esters and n-butanol.

Oral solutions are used directly. Concentrates are used orally after having been previously diluted down to the concentration for use. Oral solutions and concentrates are prepared as described above in the case of the injection solutions, with it being possible to dispense with sterile operations.

Solutions for use on the skin are dripped on, painted on, rubbed in, sprinkled on or sprayed on or applied by means of dipping, bathing or washing. These solutions are prepared as described above in the case of the injection solutions.

It may be advantageous to add thickeners during the -preparation. Thickeners are: inorganic thickeners such as bentonites, colloidal silicic acid and aluminum monostearate, and organic thickeners such as cellulose derivatives, polyvinyl alcohols and their copolymers, acrylates and methacrylates.

Gels are applied to, or painted onto, the skin or introduced into body cavities. Gels are prepared by adding sufficient thickener to solutions, which have been prepared as described above in the case of the injection solutions, to produce a clear mass having an ointment-like consistency. The abovementioned thickeners are used as thickeners.

Pour-on formulations are poured, or sprinkled, onto defined regions of the skin, with the active compound either penetrating the skin and acting systemically or being distributed on the body surface.

Pour-on formulations are prepared by dissolving, suspending or emulsifying the active compound in suitable skin-tolerated solvents or solvent mixtures. Other auxiliary substances, such as dyes, absorption-promoting substances, antioxidants, photostabilizing agents and adhesives, are added, where appropriate.

Solvents which may be mentioned are: water, alkanols, glycols, polyethylene glycols, polypropylene glycols, glycerol, aromatic alcohols, such as benzyl alcohol, phenylethanol and phenoxyethanol, esters, such as ethyl acetate, butyl acetate and benzyl benzoate, ethers, such as alkylene glycol alkyl ethers, such as dipropyleneglycol monomethyl ether and diethyleneglycol monobutyl ether, ketones, such as acetone and methyl ethyl ketone, aromatic and/or aliphatic hydrocarbons, vegetable or synthetic oils, DMF, dimethylacetamide, N-methylpyrrolidone and 2-dimethyl-4-oxymethylene-1,3-dioxolane.

Dyes are any dyes which are authorized for use in animals and which can be dissolved or suspended.

Examples of absorption-promoting substances are DMSO, spreading oils such as isopropyl myristate, dipropyleneglycol pelargonate, silicone oils, fatty acid esters, triglycerides and fatty alcohols.

Antioxidants are sulfites or metabisulfites such as potassium metabisulfite, ascorbic acid, butylhydroxy toluene, butylhydroxyanisole and tocopherol.

Examples of photostabilizing agents are substances from the benzophenone class or novantisolic acid.

Examples of adhesives are cellulose derivatives, starch derivatives, polyacrylates and natural polymers such as alginates and gelatin.

Emulsions can be used orally, dermally or as injections. Emulsions are either of the water in oil type or of the oil in water type. They are prepared by dissolving the active compound either in the hydrophobic phase or in the hydrophilic phase and homogenizing this phase with the solvent of the other phase with the aid of suitable emulsifiers and, where appropriate, other auxiliary substances such as dyes, absorption-promoting substances, preservatives, antioxidants, photostabilizing agents and viscosity-increasing substances.

Hydrophobic phases (oils) which may be mentioned are: paraffin oils, silicone oils, natural vegetable oils such as sesame oil, almond oil and castor oil, synthetic triglycerides such as caprylic/capric acid biglyceride, triglyceride mixture containing plant fatty acids of $C_{8-12}$ chain length or other specially selected natural fatty acids, partial glyceride mixtures of saturated or unsaturated, possibly also hydroxyl group-containing fatty acids, and monoglycerides and diglycerides of the $C_8/C_{10}$ fatty acids; fatty acid esters such as ethyl stearate, di-n-butyryl adipate, hexyl laurate and dipropylene glycol pelargonate, esters of a branched fatty acid of medium chain length with saturated fatty alcohols of $C_{16}$-$C_{18}$ chain length, isopropyl myristate, isopropyl palmitate, caprylic/capric acid esters of saturated fatty alcohols of $C_{12}$-$C_{18}$ chain length, isopropyl stearate, oleyl oleate, decyl oleate ethyl oleate, ethyl lactate, waxy fatty acid esters such as dibutyl phthalate and diisopropyl adipate, and ester mixtures related to the latter, and also fatty alcohols such as isotridecyl alcohol, 2-octyldodecanol, cetylstearyl alcohol and oleyl alcohol; fatty acids such as oleic acid and its mixtures.

Hydrophilic phases which may be mentioned are: water and alcohols, such as propylene glycol, glycerol and sorbitol and their mixtures.

Emulsifiers which may be mentioned are: nonionic surfactants, e.g. polyethoxylated castor oil, polyethoxylated sorbitan monooleate, sorbitan monostearate, glycerol monostearate, polyoxyethyl stearate and alkylphenyl polyglycol ethers; ampholytic surfactants, such as di-Na N-lauryl-β-iminodipropionate or lecithin; anionic surfactants, such as Na lauryl sulfate, fatty alcohol ether sulfates and monoethanolamine salt of mono/dialkylpolyglycol ether orthophosphoric acid esters; cationic surfactants, such as cetyltrimethyl ammonium chloride.

Other auxiliary substances which may be mentioned are: substances which increase viscosity and stabilize the emulsion, such as carboxymethyl cellulose, methyl cellulose and other cellulose and starch derivatives, polyacrylates, alginates, gelatin, gum Arabic, polyvinylpyrrolidone, polyvinyl alcohol, copolymers composed of methyl vinyl ether and maleic anhydride, polyethylene glycols, waxes and colloidal silicic acid, or mixtures of the listed substances.

Suspensions may be used orally or dermally or as an injection. They are prepared by suspending the active compound in a carrier liquid, where appropriate in the added presence of additional auxiliary substances such as wetting agents, dyes, absorption-promoting substances, preservatives, antioxidants and photostabilizing agents.

Carrier liquids which may be mentioned are all homogeneous solvents and solvent mixtures.

The wetting agents (dispersing agents) which may be mentioned are the above-specified surfactants.

Other auxiliary substances which may be mentioned are those specified above.

Semisolid preparations may be administered orally or dermally. They only differ from the above-described suspensions-and emulsions in their high viscosity.

In order to prepare solid preparations, the active compound is mixed with suitable carrier substances, where appropriate in the added presence of auxiliary substances, and brought into the desired form.

Carrier substances which may be mentioned are all physiologically tolerated solid inert substances. These inert substances can be inorganic substances or organic substances. Examples of inorganic substances are sodium chloride, carbonates, such as calcium carbonate and hydrogen carbonates, aluminum oxides, silicic acids, argillaceous earths, precipitated or colloidal silicon dioxide and phosphates.

Examples of organic substances are sugars, cellulose, foodstuffs and feedstuffs such as milk powder, animal meals, flours and coarse corn meals, and starches.

Auxiliary substances are preservatives, antioxidants and dyes, which have already been listed above.

Other suitable auxiliary substances are lubricants and glidants such as magnesium stearate, stearic acid, talc, bentonites, disintegration-prompting substances, such as starch or crosslinked polyvinylpyrrolidone, binders, such as starch, gelatin or linear polyvinylpyrrolidone, and also dry binders, such as microcrystalline cellulose.

Homologous Sequences

The invention also relates to polynucleotides and polypeptides from related organisms which polynucleotides and polypeptides are homologous with an EtOS22 nucleic acid and an EtOS22 polypeptide, respectively, and can be readily isolated using methods which are available in the prior art.

These methods include: PCR using degenerate primers, screening gene libraries with EtOS22, as probe, at low stringency, and screening expression libraries with the monoclonal antibody $E_2E_5$ (Sambrook and Russell, 2001).

The invention also relates to the above-described diagnostic agents, diagnostic methods, vaccines, screening methods and therapeutic agents which are based, in a manner which is analogous and evident to the skilled person, on the homologous polynucleotides or polypeptides.

Definitions

In order to improve understanding, the meaning of particular words and terms which are used in the description, the examples and -the attached claims will be explained in more detail below.

"Polynucleotidei" or "polynucleotides" is to be understood as meaning double-stranded and single-stranded DNA and double-stranded and single-stranded RNA, and cDNA, which can be present either as the coding strand or as the complementary strand, oligonucleotides, small interfering RNA (siRNA), nucleic acid analogs such as peptide nucleic acids (PNAs), locked nucleic acids (LNAs), antisense oligonucleotides, which can be synthesized, for example, by covalently bonding the 5' end of one nucleotide to the 3' end of another nucleotide by means of non-phosphodiester bonds, such as alkyl phosphonates, phosphorothioates, phosphoro-dithioates, alkyl phosphonothioates, alkyl phosphonates, phosphoramidates, Phosphate, esters, carbamates, acetamidates, carboxymethyl esters, carbonates and phosphate triesters.

The terms "homology", "identity" and "similarity" refer to sequence similarities between two peptides or between two nucleic acid molecules or polynucleotides. Homology can be determined by comparing a position in one of the sequences with the equivalent position in the other sequence. If a position in the sequence under comparison is occupied by the same base or amino acid, the two molecules are homologous at this position. The extent of the homology between sequences is a function of the number of congruent or homologous positions which the sequences share with each other. A "nonhomologous" sequence has an identity of less than 40%, preferably, however, less than 25% identity. An homology or identity can be established, inter alia, by using computer programs such as the GCG program [Devereux et al. (1983), Nucleic Acids Res. 12, 387-395].

"Homology" also exists when a polynucleotide segment is able to hybridize with another polynucleotide.

The terms "to hybridize" or "hybridization" describe the process by which a single-stranded polynucleotide enters into base pairing with a complementary DNA strand, with the ability of a single-stranded polynucleotide depending on the stringency of the hybridization conditions.

The term "stringency" refers to the hybridization conditions. "High stringency" exists when a base pairing is made more difficult. "Low stringency" exists when a base pairing is facilitated.

Stringent hybridization conditions are well known to the skilled person and are described, for example, in Sambrook et al., MOLECULAR CLONING: A LABORATORY MANUAL, 2nd ed., 1989, pp. 9.50-9.51.

In order to obtain stringent hybridization conditions, the combination of temperature and salt concentration should typically be selected. such that it is approximately 12-20° C. below the calculated melting temperature, $T_m$ of the hybrid. The skilled person is familiar with the fact that the $T_m$ of a double-stranded DNA decreases by 1-1.5° C. for every 1% decrease in identity [Bonner et al., *J. Mol. Biol.* 81, 123 (1973)]. The $T_m$ of a hybrid composed of a polynucleotide having the sequence as depicted in SEQ ID NO:1 or 3 and a polynucleotide which is at least 50%, preferably 60%, 70% 80%, 85%, 90%, 95% or 97%, identical to a polynucleotide having the sequence depicted in SEQ ID NO:1 or 3 can be calculated, for example, using Bolton and McCarthy's equation [*Proc. Natl. Acad. Sci. U.S.A.* 48, 1390 (1962)]:

$$T_m = 81.5° C. - 16.6(\log_{10}[Na^+]) + 0.41(\% \, G+C) - 0.63 \, (\% \, formamide) - 600/l,$$ in which l=length of the hybrid in base pairs.

Stringent washing conditions during the hybridization are, for example, 4×SSC at 65° C. or 50% formamide, 4×SSC at 42° C. or 0.5×SSC, 0.1% SDS at 65° C. Highly stringent washing conditions are, for example, 0.2×SSC at 65° C.

The term "plasmid" refers to an extrachromosomal genetic element. The original plasmids which are used for the present invention can either be obtained commercially or are freely available, or can be derived from such plasmids using known methods.

The term "vector" describes a polynucleotide which is used for introducing exogenous polynucleotides into host cells. A vector contains a nucleotide sequence which encodes one or more polypeptides. Vectors which are able to control the expression of the genes which they contain are termed "expression vectors".

The term "to modulate" refers both to the stimulation and to the suppression or inhibition of a biochemical process. Within the context of the present invention, "to modulate" or "modulation" means to inhibit, or an inhibition or suppression of, the activity of the EtOS22 polypeptide, which activity is of importance for the excystation of the sporozoites from the sporocysts.

EXAMPLES

Bacterial Strains and Vectors

Bacterial Strains

*E. coli* TOP10, chemically competent (Invitrogen, Groningen, NL)

F⁻ mcrA Δ(mrr-hsdRMS-mcrBC) Φ80lacZΔM15 ΔlacX74 recA1 deoR araD139 Δ(ara-leu)7697 galU galk rpsL ($Str^R$) endA1 nupG

*E. coli* TG1, electrocompetent (Stratagene, Heidelberg)

supE thi-1 Δ(lac-proAB) Δ(mcrB-hsdSM)5 ($r_k^- m_k^-$) [F' traD36 proAB $lacI^q$ZΔM15]

Vectors pG8SAET (Jacobsson and Frykberg, 1998; Zhang et al., 1999)

pCR2.1-TOPO (Invitrogen, Groningen, NL)

pcDNA3.1/V5-His-TOPO (Invitrogen, Groningen, NL)

Example 1

Isolating Genomic DNA from *Eimeria tenella*

The DNA was isolated using a method modified from that of Blin and Stafford (1976). 1×108 sporulated oocysts were sedimented at 3000 rpm for 10 min (Heraeus MULTIFUGE $3_{L-R}$) and a volume of glass beads (ø 0.45-0.5 mm) corresponding to that of the sediment was added. The oocysts and sporocyst shells were broken open by shaking with a vortex at maximum speed for 2 min, and the shells were checked under the microscope. 5 ml of extraction buffer (10 mM Tris-HCl pH 8.0; 0.1 M EDTA pH 8.0; 0.5% SDS; 20 μg of RNaseA/ml), adjusted to a proteinase K concentration of 100 μg/ml, were then added and the mixture was incubated overnight at 56° C. The DNA was extracted twice with Roti-Phenol (Roth, Karlsruhe)/chloroform and once with chloroform, after which it was precipitated with 2 vol. of absolute ethanol and 0.1 vol. of 3 M sodium acetate and sedimented by centrifugation at 13 000 rpm in a Beckman JS13.1 rotor. The sediment was washed twice with 70% ethanol and dried in air; it was then resuspended in distilled $H_2O$ ($dH_2O$), after which the concentration of the DNA was estimated in a 1% TBE agarose gel by comparing with 1 μg of EcoRI/HindIII-digested λ DNA (MBI Fermentas, St. Leon-Rot).

Example 2

Isolating Total RNA from *Eimeria tenella* and Chick Cecum

The total RNA was isolated from $3\times10^7$ oocysts or 0.3 g of chick cecum using the "Invisorb RNA kit II" (Invitek, Berlin-Buch). All the procedural steps were carried out using RNase-free material and DEPC (diethyl pyrocarbonate)-treated solutions. The oocysts were disrupted with glass beads in 500 μl of lysis solution by shaking with a vortex, while the intestinal tissue was comminuted with an Ultraturrax in 2 ml of lysis solution. The supernatant was in each case used for isolating the RNA and all further procedural steps were in accordance with the manufacturer's instructions. The total RNA, dissolved in DEPC $H_2O$, was then determined photometrically.

Example 3

Preparing Plasmid DNA

Plasmid DNA was prepared from stationary 3 ml of 50 ml cultures of *E. coli* TG1 or *E. coli* TOP10. A single colony was used to inoculate LB medium in the added presence of the appropriate antibiotic and the culture was incubated, with shaking at 280 rpm, overnight at 37° C. The NucleoSpin plasmid kit (Macherey-Nagel, Düren) or the Plasmid Midi kit (Qiagen, Hilden) was used for isolating the plasmid. The plasmid DNA was purified in accordance with the instructions of the respective manufacturer.

Example 4

Determining Nucleic Acid Concentration

The concentration of the nucleic acid was determined photometrically in a DU 640 spectrophotometer (Beckmann, Munich). Its concentration and purity were calculated as described by Sambrook et al. (1989). Restriction fragments which were to be used as probes for Southern and Northern blotting were assessed in a 1% TBE agarose gel by comparing them with 1 µg of EcoRI/HindIII-digested λ DNA (MBI Fermentas, St. Leon-Rot).

Example 5

Restricting and Electrophoretically Separating DNA

DNA was restricted with restriction endonucleases in accordance with the manufacturer's instructions and in the buffer which was recommended for the enzyme concerned. As a rule, the incubation was for 3 h at 37° C.

DNA fragments were separated electrophoretically by the method of Sambrook et al. (1989) in a horizontal flat bed chamber. To do this, use was made of 0.6-2% agarose gels which were poured using TBE buffer or TAE buffer and in the added presence of 0.5 µg of ethidium bromide/ml. The DNA molecules, which were stained with ethidium bromide, were then compared, on a transilluminator, with DNA length standards which had been separated in parallel. 1 µg of pUC-Mix markers was used for fragments<1 kb while 1 µg of EcoRI/HindIII-digested λ DNA was used for larger fragments (both from MBI Fermentas, St. Leon-Rot).

Example 6

Isolating DNA Fragments from Agarose Gels

DNA fragments were isolated from agarose gels either using agarase (Roche Molecular Biochemicals, Mannheim), by means of digesting low melting point agarose (Biozym, Hess. Oldendorf) which had been poured, as a window gel, in a TAE agarose gel of the same percentage, or using the Nucleospin Extract 2 in 1 kit (Macherey-Nagel, Düren). In both cases, the desired fragment was excised under longwave UV light and isolated in accordance with the manufacturer's instructions. In order to determine the concentration of the DNA 1/10 of the sample volume was then separated in a control gel and estimated by comparison with the DNA length standard.

Example 7

Chemically Transforming E. coli

Chemically competent E. coli TOP10 (Invitrogen, Groningen, NL) were transformed with recombinant plasmids in accordance with the manufacturer's instructions. After the transformed cells had been plated out on selection agar, and incubated overnight at 37° C., transformants could be isolated and analyzed by restriction digestion.

Example 8

Constructing an Eimeria tenella Genomic Expression Library a) Fragmenting Genomic DNA, and Blunt-end Reaction 25 µg of Eimeria tenella genomic DNA were fragmented, in a volume of 4 ml, using a Sonotrode MS73 at 40% instrument workload, for 10×30 s and while cooling in an ice-cold water bath. These fragments, which were between 100 and 800 bp in size, were then precipitated, resuspended in 60 µl of dH$_2$O and separated in a 1.2% agarose gel which possessed a low melting point agarose window of the same percentage and which did not contain ethidium bromide. The fragments, which were isolated by agarase digestion, were purified through S-400 HR Microspin columns (Amersham Pharamacia Biotech, Freiburg) in accordance with the manufacturer's instructions.

The following reaction mixture was prepared for the blunt-end reaction: 75 µl of purified DNA fragments, 1 mM dNTP mix, 10 U of AccuTherm DNA polymerase (GeneCraft, Münster) and 1×AccuTherm buffer, made up to 100 µl with dH$_2$O. This reaction mixture was incubated at 72° C. for 30 min, after which it was extracted with phenol/chloroform and the fragments were resuspended in 100 µl of dH$_2$O. 2 µl of this suspension were separated in a test gel for the purpose of assessing concentration.

b) Dephosphorylating pG8SAET

20 µg of pG8SAET were incubated with 40 U of SnaBI (Promega, Heidelberg) at 37° C. for 3 h. After that, 4 U of shrimp alkaline phosphatase (USB, Bad Homburg) were added to the restriction mixture and the whole was incubated at 37° C. overnight. After 10 min of heat inactivation at 65° C., the linearized and dephosphorylated vector was isolated from an 0.8% low melting point agarose window gel by means of digesting with agarase.

c) Ligating DNA

300 U of T4 DNA ligase HC (MBI Fermentas, St. Leon-Rot) were used to ligate 8 µg of genomic DNA fragments and 5 µg of linearized and dephosphorylated pG8SAET, at 16° C. for 48 h, in a total volume of 100 µl. After that, the ligase was heat-inactivated at 65° C. for 10 min and the recombinant vector molecules were precipitated by adding 20 µg of glycogen. The sediment was resuspended in 100 µl of dH$_2$O, 1.5 µl of which suspension were used for each electrotransformation.

d) Electrotransforming E. coli

50 µl volumes of E. coli TG1 were in each case electrotransformed with 1.5 µl of ligation mixture, in 0.1 cm electroporation curvets (BIO-RAD, Munich) and at a field strength of 17 kV/cm, at 200Ω and 25 µF in a Gene Pulser (BIO-RAD, Munich) in accordance with the manufacturer's instructions. The number of transformants was determined and the recombinant cells were stored at −80° C. in the form of glycerol stocks.

A representative genomic DNA library of the parasite was constructed in the phagemid vector pG8SAET. This library comprises 4.7×10$^6$ independent clones (95% recombinant) having a mean insert size of 450 bp, with this giving a 7.3-fold representation of the Eimeria tenella genome.

Example 9

Phage Display and Phase Panning a) Preparing and Purifying Recombinant Phagemids 200 µl of each of the glycerol stocks were inoculated into 20 ml of ampicillin-containing LB medium (50 µg/ml) and the culture was incubated overnight at 37° C. and 280 rpm. 1 ml of this culture was then used to inoculate 100 ml of ampicillin-containing LB medium, with this culture being incubated up to an OD$_{600}$=0.5 and then infected with 500 µl (1×10$^{11}$ pfu) of R408 helper phages (Promega, Heidelberg). Following renewed incubation at 37° C. and 280 rpm overnight, the cells were sedimented at 5000 rpm for 10 min and the supernatant was sterilized by filtration; the phagemids were then concentrated using Vivaspin 20 concentrators (Sartorius AG, Göttingen) in accordance with the manufacturer's instructions.

b) Coating DYNABEADS

A hybridoma culture supernatant of the monoclonal antibody (Mab) $E_2E_5$ (Mouafo et al., 2002). which had been concentrated 50-fold by means of ultrafiltration (100 kDa MWCO), was used for coating Pan Mouse IgG DYNABEADS (Deutsche Dynal GmbH, Hamburg). 20 µg of concentrated total protein, having a content of approx. 5% $E_2E_5$ MAb, were used per mg of DYNABEADS and the mixture was incubated, with rotation, overnight at 4° C. Unbound proteins and immunoglobulins were removed by washing 3 times with PBS (8 g of NaCl; 0.2 g of KCl; 1 g of $Na_2HPO_4 \times 2$ $H_2O$; 0.15 g of $NaH_2PO_4 \times H_2O$; 0.2 g of $KH_2PO_4$, pH 7.4 made to 1l with $H_2O$)/0.1% BSA, and the DYNABEADS were then used in the binding reaction.

c) Binding Reaction, Washing Steps and Elution

In the binding reaction, 50 µl ($2 \times 10^7$) of DYNABEADS, with or without Mab $E_2E_5$ on the surface, were incubated, overnight at 4° C. and while rotating, with 200 µl of phagemid concentrate in a volume of 400 µl in PBS/0.1% BSA. After the DYNABEADS have been washed 10 times, weakly binding phagemids were discarded after a 15-minute rotating incubation in 400 µl of elution buffer (50 mM sodium citrate; 150 mM NaCl, pH 4.5), and the phages which eluted in pH 1.8 elution buffer were treated with 40 µl of neutralization buffer (2 M Tris-HCl, pH 8.6) and used for determining the titer and reinfection.

d) Titer Determination and Reinfection

Each eluate was used for reinfecting 10 ml of *E. coli* TG1 which were in the logarithmic phase of growth. After having been incubated at 37° C. and 40 rpm for 0.5 h, the cells were sedimented and then resuspended in 400 µl of ampicillin-containing LB medium; they were then sown on ampicillin-containing LB agar plates for the titer determination and/or for amplification. For a further round of phase panning, these plates were rinsed off, after 18 h, with ampicillin-containing LB medium and the bacteria were infected, in a 50 ml culture, with 100 µl of R408 helper phages. Following incubation at 37° C. and 280 rpm overnight, the phagemids were concentrated as described and used for new binding reactions.

e) Detecting E Tag-expressing Clones

For the purpose of isolating E tag-expressing clones, approx. 100 colony-forming units (cfu) were sown, following several rounds of phase panning, on ampicillin-containing agar plates and transferred to a nitrocellulose membrane (Schleicher and Schuell, Dassel). The cells adhering to the membrane are lysed overnight in 6 ml of lysis buffer (100 mM Tris-HCl, pH7.8; 150 mM NaCl; 5.mM $MgCl_2$; 1.5% BSA; 1 µg of DNase I/ml; 40 µg of Lysozyme/ml), after which cell residues are removed by washing 3 times with PBS/0.05% Tween-20 and nonspecific binding sites on the membrane are saturated by blocking for 1 h with 1× RotiBlock solution (Roth, Karlsruhe). The membrane was then incubated, at room temperature (22° C.) for 2 h, with the mouse anti-E tag primary antibody (Amersham Pharmacia, Freiburg), which was diluted 1:500 in 1× RotiBlock. Unbound antibodies were removed by washing 3 times for 0.5 h. An alkaline phosphatase (AP)-coupled goat anti-mouse IgG was used, in a 1:2000 dilution, as the secondary antibody. After 3 further washing steps, the membrane was equilibrated for 2 min in detection buffer (100 mM Tris-HCl, pH 9.5; 100 mM NaCl) and bound secondary antibodies were detected by generating chemiluminescence with the aid of CDP star (Roche Molecular Biochemicals, Mannheim), which was diluted 1:100 in detection buffer. The exposure was for 2-10 min, at 22° C., on ECL Hyperfilm (Amersham Pharmacia, Freiburg).

f) Phage Panning Compared with $E_2E_5$ MAb Enrichment of Specifically Binding Clones The monoclonal antibody (MAb) $E_2E_5$ was bound to the surface of Pan Mouse IgG DYNABEADS and used in the phage panning. Pan Mouse IgG DYNABEADS without any further antibody were used as the negative control. After 3 rounds of phage panning, binding clones were enriched 362-fold as compared with the negative control. Those clones expressing E tag were analyzed with the $E_2E_5$ MAb in Western blots. Of the 62 E tag-expressing clones which were isolated, 6 (A14, A17, A45-A47 and A62) were recognized by $E_2E_5$ MAb in Western blots. All the fusion proteins which were detected exhibited the same migration behavior in SDS-PAGE, with a molecular weight of approx. 14 kBa. These fusion proteins were composed of 125 AA, 48 AA of which could be attributed to tie cloned-in "A17" insert.

Example 10

Polymerase Chain Reaction (PCR)

All the PCRs were cam ed out in a PTC-200 Gradient Cycler or PTC-150 MiniCycler. from MJ Research (Biozym, Hess. Oldendorf).

Synthetic Oligonucleotides (Primers)

All the PCR primers were synthesized by MWG Biotech (Ebersbach).

| Primer (RT-PCR) | SEQ ID NO |
|---|---|
| A17-22-up | SEQ ID NO. 4 |
| A17-112-lo | SEQ ID NO. 5 |
| A17-f-length-64-up | SEQ ID NO. 6 |
| A17-f-length-1176-lo | SEQ ID NO. 7 |
| EtACTIN-up | SEQ ID NO. 8 |
| EtACTIN-lo | SEQ ID NO. 9 |

| Primer (RACE-PCR) | SEQ ID NO |
|---|---|
| A17-22-up | SEQ ID NO. 4 |
| A17-max-90-up | SEQ ID NO. 10 |
| A17-max-150-up | SEQ ID NO. 11 |
| A17-112-lo | SEQ ID NO. 5 |
| A17-max-533-lo | SEQ ID NO. 12 |
| A17-max-631-lo | SEQ ID NO. 13 | a) RT-PCR

RT-PCR comprises the reverse transcription of total RNA followed by PCR for the purpose of amplifying DNA sequences using sequence-specific primers. The composition of the reaction mixture for the RT was as follows, in a total volume of 50 µl: 3.5 µg of total RNA, 80 U of RNasin ribonuclease inhibitor (Promega, Heidelberg), 0.4 mM dNTP mix, 50 U of AMV reverse transcriptase, 1×AMV buffer (all from Roche Molecular Biochemicals, Mannheim), 5 mM DTT and 2.5 mM of random hexamer primers as molecules for starting the cDNA synthesis. An incubation at 22° C. for 10 min was followed by synthesis of the cDNA, at 42° C. and 55° C. for in each case 30 min. The enzyme was heat-inactivated at 95° C. for 5 min. For each reverse transcription, two further reactions, i.e. without reverse transcriptase and without RNA template, respectively, were carried out as negative controls.

¹/₁₀ volume of the reverse transcriptase reactions were used, in a total volume of 50 µl, as template for the PCR which followed. The following PCR systems, in each case using 0.4 µM of the two sequence-specific primers, were used, in accordance with the manufacturer's instructions, for the amplification: "Triple Master PCR system" (Eppendorf), "Platinum Pfx DNA polymerase" (Invitrogen, Groningen, NL) and "High Fidelity PCR system" (Roche Molecular Biochemicals, Mannheim). The initial denaturation at 94° C. for 2 min was followed by 35 cycles composed of 15 s of denaturation at 94° C., 30 s of annealing at 63° C. and 2 min of chain extension at 72° C. A terminal elongation at 72° C. for 10 min completed the reaction. ⅕ volume of this reaction was fractionated, for control purposes, in a TBE agarose gel of the appropriate percentage.

b) 5'- and 3'-RACE-PCR

Total RNA from sporulated *Eimeria tenella* oocysts was employed as the starting material for the 5'- and 3'-RACE-PCR, which was carried out using the "5'/3' RACE kit" (Roche Molecular Biochemicals, Mannheim). The cDNA synthesis, the tailing reaction (only in the case of 5'-RACE), and amplification of the cDNA using sequence-specific primers, were carried out in accordance with the manufacturer's instructions. This was then followed by one, in the case of the 5'-RACE, and two, in the case of the 3'-RACE, further nested PCRs in order to increase the amplification of the 5' and 3' ends. A17-max-631-lo (cDNA synthesist, A17-max-533-lo (amplification of the dA-tailed cDNA) and A17-112-lo (nested PCR) were used as sequence-specific primers in the 5'-RACE, while A17-max-90-up (amplification of cDNA), A17-max-150-up (1$^{st}$ nested PCR) and A17-22-up (2$^{nd}$ nested PCR) were used as such primers in the 3'-RACE. The RACE-PCR products, which were separated in a 2% agarose gel, were transferred, using the method of Chomczynski (1992), to a neutral Hybond-N nylon membrane (Amersham Pharmacia Biotech, Freiburg), hybridized with a radioactively labeled probe and then used for exposing Kodak Biomax MS X-ray films. The specific RACE-PCR products which were identified in this way were cloned, isolated and sequenced.

Example 11

Cloning PCR Products

The TOPO TA cloning kit and the pcDNA3.1/V5-His TOPO TA expression kit (Invitrogen, Groningen, NL) were used for cloning PCR products. The PCR products 30 were isolated from agarose gels using the NucleoSpin Extract 2 in 1 kit (Macherey-Nagel, Düren) and then incubated, at 72° C. for 0.5 h, with 5 U of Taq DNA polymerase (Promega, Heidelberg), 1× Taq DNA polymerase buffer and 0.4 mM of dNTP mix. The PCR products, which were adenylated at the 3' end by the terminal transferase activity of Taq DNA polymerase, were purified for a second time using the NucleoSpin Extract 2 in 1 kit and then used in the TOPO TA cloning in accordance with the manufacturer's instructions.

Example 12

DNA Sequence Analysis

Cloned DNA was sequenced nonradioactively in accordance with the chain termination method of Sanger et al. (1977) and using an automated LI-COR 4000 DNA sequencer supplied by MWG Biotech (Ebersbach). The sequencing was carried out using 5'-mD-800-coupled primers for the pG8SAET vector (MWG Biotech, Ebersberg) and using 5'-IRD-800-coupled standard primers (LI-COR Bioscience, Bad Homburg).

5'-IRD-800-coupled Primers

| 5'-IRD-800 primer | SEQ ID NO |
|---|---|
| pG8SAET-up | SEQ ID NO. 14 |
| pG8SAET-lo | SEQ ID NO. 15 |
| pG8SAET-seq-up-140 | SEQ ID NO. 16 |
| A17-sequint-27-up | SEQ ID NO. 17 |
| A17-sequint-44-up | SEQ ID NO. 18 |
| A17-sequint-385-lo | SEQ ID NO. 19 |
| A17-sequint-351-lo | SEQ ID NO. 20 |
| M13 reverse | SEQ ID NO. 21 |
| M13 forward | SEQ ID NO. 22 |
| T7-Promotor | SEQ ID NO. 23 |
| BGH reverse | SEQ ID NO. 24 | a) Sequencing using Thermo Sequenase

The Thermo sequenase primer cycle sequencing kit (Amersham Pharmacia Biotech, Freiburg), and primer coupled to the infrared fluorescent dye IRD-800 (MWG Biotech, Ebersbach), were used for the sequencing reaction. For each reaction, 1.5 µg of plasmid DNA and 2-4 µl of 5'-IRD-800-coupled primer (1 pmol/µl) were mixed in a total volume of 13 µl and in each case 3 µl of this mixture were added to in each case 3 µl of the respective A, C, G or T nucleotide mix, with these mixtures then being in each case overlaid with 10 µl of mineral oil. The sequencing reaction then took place in a PTC 100 thermocycler (MJ Research, Biozym, Hess. Oldendorf). In the reaction, a 2-minute denaturation at 94° C. was followed by 30 cycles of denaturation (94° C. for 30 s), annealing (55° C. for 30 s) and strand synthesis (72° C. for 1.5 min). The reactions were stopped by adding 6 µl of formamide loading buffer. Immediately before loading the sequencing reaction onto the sequencing gel, the reaction samples were denatured at 72° C. for 3 min and, immediately after that, stored on ice while being protected from light. The fluorescence-labeled chain termination fragments were separated, in 1×TBE buffer and at 1500 V and 50° C., in 40 cm-long, 0.25 mm-thick 6% gels composed of modified polyacrylamide (Ultra Pure Sequagel XR, National Diagnostics; Atlanta, USA) containing 8 M urea and detected, in real time, using a laser photomultiplier unit. The sequences were analyzed using the LI-COR ImagIR 4.0 software base (MWG Biotech, Ebersbach).

b) Computer Analysis of Sequence Data

The data obtained by the sequence analysis were firstly processed using the Molecular BioComputing Suite (Muller et al., 2001) and Sequences 3.0 programs, and the deduced protein sequences were determined. The BLAST (Altschul et al., 1990) and omniBLAST programs were used for the database searches, that is the comparison with already known sequences in the EMBL and SwissProt databases or with the *Eimeria tenella* genome project data. Two or more DNA pr protein sequences were aligned using the BLAST 2 sequences (Tatusova and Madden, 1999), CLUSTALW (www.ebi.ac.uk) (Thompson et al., 1994) and DIALIGN (Morgenstern et al., 1998; 1999) programs. In addition, the SignalP (Nielsen et al., 1997) and Clone Manager 5 programs were used for identifying signal peptides and, respectively, planning clonings and restrictions and for searching for open reading frames.

Example 13

Preparing Protein Exacts from *E. coli*

2 ml of *E. coli* TG1 were sedimented from a stationary overnight culture, washed 1× with $dH_2O$ and resuspended in 300 µl of $dH_2O$. 100 µl of 4× RotiLoad buffer (Roth, Karlsruhe) were added and the sample was denatured for 5 min in boiling water. The genomic DNA in the mixture was then fragmented by means of a short ultrasonic treatment and in each case 10 µl of this sample were loaded onto an SDS polyacrylamide gel.

Example 14

Electrophoretically Separating Proteins in Polyacrylamide Gels, and Western Blotting a) SDS-PAGE The, method of Lämmli (1970) was used to separate protein extracts under denaturing conditions in discontinuous polyacrylamide gels. The Mini-PROTEAN II electrophoresis cell apparatus (BIO-RAD, Munich) was used for this purpose. In this system, the gel size is 8×10 cm. Separating gels containing 15% polyacrylamide were used. The concentration of the stacking gels was uniformly 4.5% polyacrylamide. Separation took place at 40 mA for approx. 2-2.5 h. 5 µl of the prestained SDS molecular weight marker mix (Sigma, Deisenhofen) were used as the molecular weight standard.

b) Protein Transfer onto Nitrocellulose Membrane

The proteins which were separated in the SDS-PAGE were blotted onto Protran BA 85 nitrocellulose membranes (Schleicher and Schuell, Dassel) using the semidry method (Kyhse-Anderson, 1984). This method used a continuous buffer system (Lihme and Schafer-Nielsen, 1986) in which only the layers of Whatman paper (Whatman Ltd., Maidstone, England), which were soaked in blotting buffer, between two graphite plates (Biometra Fast Blot, Göttingen) served as the buffer reservoir. A homogeneous electrical field, in which the proteins were transferred, at a current strength of 60 mA and for 2 h from the SDS polyacrylamide gel to the nitrocellulose membrane, was generated between these graphite plates. In order to check the transfer, the nitrocellulose membrane was stained reversibly, after the blotting, with Ponceau S (0.2% Ponceau S in 3% trichloroacetic acid) and then destained once again using $dH_2O$.

c) Immunodetection

The nitrocellulose membrane was rolled up inside a 50 ml centrifuge tube (Falcon, Becton Dickinson, Sunnyvale, Calif., USA) and incubated, for 1 h and while being rotated, with 10 ml of 1× RotiBlock solution (Roth, Karlsruhe) in order to saturate nonspecific binding sites. After that, this blocking solution was replaced with 50 µl of 50-fold concentrated hybridoma culture supernatant of the monoclonal antibody $E_2E_5$ (primary antibody) in 10 ml of 1× RotiBlock solution. After having been incubated at 22° C. for 2 hours, the membrane was washed 3× for a total of 0.5 h with PBS/0.05% Tween-20 in order to remove the unbound excess of primary antibody. The secondary antibody, i.e. goat anti-mouse IgG which was coupled to horseradish peroxidase (HRP) (Jackson Immuno Research Laboratories, West Grove, USA) and which was diluted 1:4000 in 10 ml of 1× RotiBlock solution, was then added for 1 h. The membrane was then washed once again 3× for a total of 0.5 h with PBS/0.05% Tween-20. The bound antibodies were now detected by using the ECL Western blotting detection system (Amersham Pharmacia, Freiburg) to generate chemiluminescence following the method of Roswell and White (1978). For this, equal volumes of the detection reagents 1 and 2 were mixed and added to the membrane (0.125 ml/cm²). After 1 min, the liquid was removed and the membrane was rinsed 1× briefly with PBS/0.05% Tween-20; it was then laid, free of air bubbles, between two overhead transparency films. The exposure was effected, for 2-5 min at 22° C., on ECL Hyperfilm (Amersham Pharmacia, Freiburg).

Example 15

Radioactively Labeling DNA

The radioactive labeling of DNA depended on the size of the probes which were employed. DNA fragments>800 bp were labeled by means of random priming with $[\alpha^{32}P]dCTP$, following the method of Feinberg and Vogelstein (1984). The Megaprime DNA labeling kit (Amersham Pharmacia Biotech, Freiburg) was used, in accordance with the manufacturer's instructions, for this labeling reaction. 40 ng of DNA and 50 µCi of $[\alpha^{32}P]dCTP$ (10 µCi/µl, spec. activity>3000 Ci/mmol) were used per assay.

Very small DNA fragments, such as oligonucleotides, were radioactively labeled with $[\gamma^{32}P]ATP$. In this reaction, T4 polynucleotide kinase (MBI Fermentas, St. Leon-Rot) catalyses the transfer of the $[\gamma^{32}P]ATP$ to the 5' OH group of the DNA. 20 ng of oligonucleotide and 100 µCi $[\gamma^{32}P]ATP$ (10 µCi/µl, spec. activity>4500 Ci/mmol) were used. At the end of the labeling reaction, unincorporated nucleotides were separated off using the NucleoSpin extract 2 in 1 kit (Macherey-Nagel, Düren). The DNA which had been labeled and purified in this way was denatured for 10 min before being used for the hybridization.

Example 16

Southern Blotting: Transferring DNA to Membranes, and Hybridizing

This technique was used to transfer both PCR products and genomic DNA onto a neutral Hybond-N nylon membrane (Amersham Pharmacia Biotech, Freiburg). The genomic DNA had previously been digested with a variety of restriction endonucleases (10 µg per restriction assay) and separated overnight, at 20 mV, in an 0.6%, 14 cm-long agarose gel. The blotting was carried out, in accordance with the method of Chomczynski (1992), by means of downwardly directed capillary transfer in alkaline transfer buffer (3 M NaCl, 8 mM NaOH, pH 11.40-11.45) for 2 h or overnight. Prior to the transfer, the DNA in the gel was denatured in 1.5 M NaCl, 0.5 M NaOH for 1 h and then incubated in transfer buffer for 10 min. After the transfer had taken place, the membrane was neutralized with 0.2 M sodium phosphate buffer (pH 6.8) for 15 min and then baked at 80° C. for 20 min. The DNA on the membrane was now used for hybridizing with radioactively labeled probes. However, the membrane was first of all incubated at 60° C. for 3 h in prehybridization solution. This solution was then replaced with the hybridization solution. After the radioactively labeled probe had been added, hybridization then took place overnight at 60° C. A 20×SSC stock solution (3 M NaCl; 0.3 M sodium citrate, pH 7.0 in $H_2O$) was used for the washing buffer. The membrane was washed consecutively in 2×SSC, 0.1% SDS for 30 min and in 1×SSC, 0.1% SDS for from 30 min to 2 h. The membrane was exposed on Kodak Biomax MS X-ray films at −80° C. using an intensifying screen.

Example 17

Electrophoresing RNA, and Northern Blotting

All the procedural steps for electrophoresing RNA were carried out under RNase-free conditions using buffers which had been treated with 0.1% DEPC and then autoclaved. The RNA was denatured with glyoxal and DMSO, and then separated electrophoretically, as described in Sambrook et al. (1989). 5.4 µl of deionized 6 M glyoxal, 16.0 µl of DMSO and 3 µl of 0.1 M sodium phosphate buffer (pH 7.0) were added to 20 µg of RNA, which was in a volume of 5.4 µl, and the whole was incubated at 50° C. for 1 h. After that, 6 µl of glyoxal gel loading buffer (10 mM sodium phosphate, pH 7.0; 50% glycerol; 0.25% bromophenol blue) were added on ice. The separation was effected, at 3-4 V/cm, in a 1.2% agarose gel in 10 mM sodium phosphate buffer (pH 7.0). The RNA was blotted onto a neutral Hybond-N nylon membrane (Amersham Pharmacia Biotech, Freiburg) using a downwardly directed capillary blotting technique and employing an alkaline transfer buffer (3 M NaCl, 8 mM NaOH, pH 11.40-11.45) (Chomczynski, 1992). The membrane was neutralized in 0.2 M sodium phosphate buffer (pH 6.8) for 15 min and finally baked at 80° C. for 20 min. For the purpose of assessing size, 10 µg of EcoRI/HindIII-digested λ DNA (MBI Fermentas, St. Leon-Rot) were glyoxylated and separated in parallel with the RNA. After the electrophoresis, the lanes containing λ DNA were separated from the remainder of the gel, washed in 50 mM NaOH for 20 min in order to remove the glyoxal, neutralized in 50 mM sodium phosphate buffer (pH 7.0) for 15 min and finally stained with 0.5 µg of ethidium bromide/ml in the same buffer. The hybridization was carried out as described for the Southern blotting but under more stringent conditions, i.e. at 65° C. and using 0.1×SSC, 0.1% SDS as the second washing buffer.

Example 18

Sequencing the EtOS22 cDNA

The phage clones whose fusion proteins were recognized by the $E_2E_5$ MAb in the Western blotting were analyzed by means of DNA sequencing. Based on this known sequence (underlaid in dark gray), 5'- and 3'-RACE-PCR were used to amplify the 3' end of this gene and the majority of the 5' end, with 5'-RACE being used to extend the 5' end by 224 bp. While the reading frame still remained continuous, the start codon (ATG), with which an open reading frame (ORF) begins, was missing. In order to use RT-PCR to amplify the complete ORF of this gene, two new primers were constructed. on the basis of data from the *Eimeria tenella* genome project: A17-f-length-64-up and A 17-f-length-i 1176-lo, which are underlined in the sequence, gave rise to a PCR product of 1106 bp. In this way, the complete open reading frame was amplified. The primers hybridized in the 5'-UTR and 3'-UTR, respectively, of the cDNA. There is an upstream stop codon between the 5' primer and the ATG start codon, with this ensuring that the PCR product contains the complete open reading frame. The EtOS22 cDNA possesses an ORF of 594 bp, or 198 AA, and ends in position 677 with a TAA stop codon. The 3'-UTR encompasses 506 bp. FIG. 1 gives the complete sequence of the cDNA for EtOS22; however, the length of the 5'-UTR has not yet been determined.

Example 19

Characterizing EtOS22

The SignalP V1.1 program (Nielsen et al., 1997) identifies a signal peptide of 18 AA (underlaid in pale gray in the sequence) at the N-terminal end of the protein. The site of cleavage between the signal peptide and the mature protein probably lies between positions 18 and 19 (AVA-AD). Consequently, the size of the mature protein is 180 AA. This gives a theoretical molecular weight of 21 039.7 Da without the signal peptide or 22 830.9 Da with the signal peptide. A striking feature is the frequency of particular AAs in the precursor protein (or in the mature protein): histidine (H) 23.2% (25.6%), proline (P) 17.2% (18.9%), alanine (A) 8.6% (6.7%) and glutamine (Q) 7.6% (8.3%). Histidine and proline together make up more than 40% of all the amino acids in the protein.

Example 20

Expression of EtOS22 in *Eimeria tenella*

RT-PCRs and Northern blots were carried out, using sequence-specific primers and radioactively labeled probes, respectively, for the purpose of analyzing the pattern of expression of EtOS22 in *Eimeria tenella* by means of detecting the corresponding transcript. cDNA from 4 different parasite stages was used for the RT-PCRs: from sporulated oocysts and from intracellular stages at 72 h, 137 h and 148 h after the infection of the chicken, with total RNA for these stages being isolated from infected chicken ceca. RT-PCR products were successfully amplified at 137 and 148 h after the infection (gamogony) and in the oocyst stage but not at 72 h after the infection (schizogony). Accordingly, the gene is still not being transcribed at 72 h after the infection, on the other hand, transcription takes place from no later than 137 h after the infection, and onwards, and still takes place in the sporulated oocysts (FIG. 2).

Figure 3:
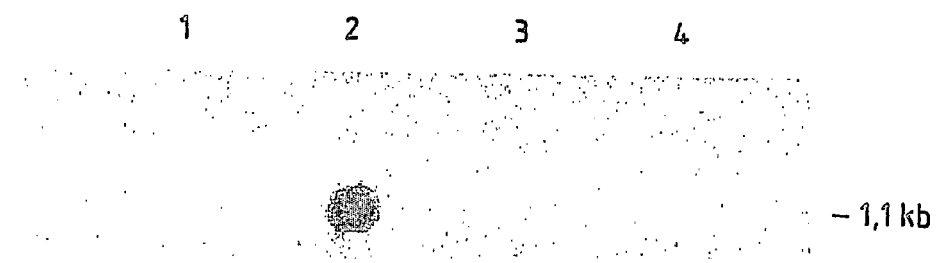
FIG. 3 shows the Northern blot analysis for EtOS22. Total RNA from sporulated oocysts (1), total RNA from infected chick cecum 137 h (2) and 148 h (3) after infection, and also total RNA from uninfected chick cecum as the negative control (4), were separated by gel electrophoresis and blotted. The blot was hybridized with the radioactively labeled 3'-RACE-PCR product (816 bp), which begins in position 385.

The Northern blotting showed that there was a very marked peak of expression at 137 h after the infection. When this method was used, it was scarcely possible, or no longer possible, to detect the EtOS22 MRNA transcript after 148 h and in the oocysts (FIG. 3). In addition to this, Northern blotting indicated that the size of the complete MRNA transcript was approx. 1.1 kb. This tallies very well with the size of the cloned cDNA.

Example 21

Locating the Oocyst Sporocyst Protein (EtOS22) in *Eimeria tenella* a) Immunofluorescence $3×10^7$ sporulated oocysts were sedimented at 14 000 rpm for 2 min and washed 1× with PBS; they were then shaken vigorously for 2 min, using a vortex, with a volume of glass beads (ø 0.45-0.5 mm) corresponding to that of the sediment until a portion of the oocysts and sporocysts present in the sample had been ruptured (checked microscopically). These cells and cell debris were sedimented and then resuspended in cold methanol (at −20° C.), after which they were incubated at 22° C. for 10 min. After a further washing step, they were resuspended, at 22° C. for 10 min, in PBS/0.1% Triton X 100. They were then repeatedly washed thoroughly with PBS before nonspecific binding sites in the cell material were saturated, at 22° C. for 1 h, by means of incubating, while rotating, in blocking buffer (PBS/1% BSA). After that, 25 μl of the 50-fold concentrated hybridoma culture supernatant of the $E_2E_5$ monoclonal antibody (primary antibody) were added in 1 ml of blocking buffer and the mixture was incubated, with rotation, for 2 h. The excess of primary antibody was removed by washing 3 times with PBS for a total of 0.5 h before the cell material was incubated, for 1 h, while rotating and while being protected from light, with the Alexa Fluor 488 goat anti-mouse IgG (H+L) (MoBiTec GmbH, Göppingen) secondary antibody. After having been washed 2 times with PBS, the cell pellet was resuspended in Mowiol (Polyscience Inc., Niles, Ill., USA); 15 μl of this suspension were then placed on a microscope slide, covered with a cover slip so as to exclude air bubbles and stored at 4° C. in the dark.

b) Confocal Laser Scanning Microscopy

A Zeiss IM 35 microscope (Zeiss, Oberkochen) fitted with a Leica CLSM TCS NT attachment (Leica Lasertechnik, Heidelberg), Version 1.5.451, was used for the confocal laser scanning microscopy. An argon laser was used, at a wavelength of 488 nm, to stimulate the Alexa 488 dye to fluoresce. Z series of optical sections through oocysts and sporocysts were scanned with a resolution of 1.024×1.024 pixels. Adobe Photoshop 6.0 and Corel Draw 10.0 for Windows were used for analyzing the results.

The immunofluorescence recorded against EtOS22 in *Eimeria tenella* oocysts (FIG. 5.1) and sporocysts (FIGS. 5.2 and 5.3) first of all confirmed the studies of Mouafo et al. (2002). The fact that the oocyst wall was stained in ruptured oocysts but not in intact oocysts, suggests that the EtOS22 is located on the inner wall. In addition to this, distinct fluorescence signals appeared in the region of the sporocyst Stieda body. This structure is closely associated with excystation, i.e. the hatching of the two sporozoites from the sporocysts. The fact that it is only sporocysts which are already ruptured which exhibit these fluorescence signals indicates that EtOS22 is a component of structures which are located in the interior of the sporocysts and is not a component of the outer sporocyst shell.

Example 22

Sporozoite Excystation

In order to obtain fresh oocysts, 2-3-week-old chicks were infected with approx. 5000 sporulated *Eimeria tenella* oocysts using a probang. On the 7$^{th}$ day after the infection, the animals were sacrificed and the content of the ceca were collected in a 2% solution of potassium dichromate. While being stirred at approx. 28° C., the oocysts sporulated within 48 h. In order to obtain sporocysts, the oocysts were disrupted using a Potter. To do this, about 1.5 ml of concentrated oocyst suspension were pipetted into the Potter vessel and homogenized at 1300 rpm until all the oocysts were fractured (checked microscopically).

The sporocysts which had been liberated were collected in a 50 ml centrifuge tube (Falcon, Becton Dickinson, Sunnyvale, Calif., USA) and, centrifuged at 2000 rpm for 10 min. The sediment was resuspended in 25 ml of PBS and stored at 4° C. overnight in the added presence of 10 μg of Baytril/ml (BAYER, Leverkusen). On the following morning, the suspension was sedimented and the sporocysts were resuspended in a mixture consisting of 1 ml of bile and 20 ml of PBS-trypsin which had been sterilized by filtration. In each case 2 ml aliquots this mixture, with or without the addition of 100 μl of the 50-fold concentrated hybridoma culture supernatant of the $E_2E_5$ monoclonal antibody, were used for parallel excystation experiments. These mixtures were incubated for 5 h in an incubator whose temperature was set to 41.5° C. Subsequently, a Bürker chamber was used to determine, in the case of both mixtures, the number of free sporozoites and of unhatched sporozoites in the sporocysts.

Example 23

Inhibiting Sporozoite Excystation

Figure 6:
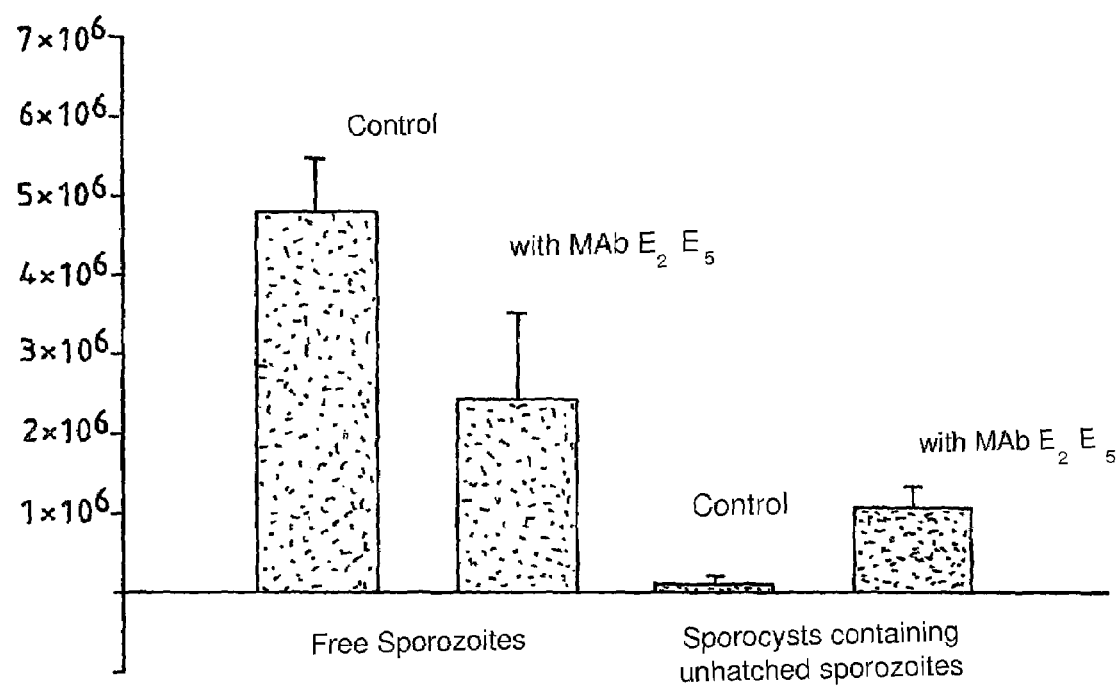
FIG. 6 shows that EtOS22 is a target for inhibiting *E. tenella* excystation. Following parallel excystation experiments, the number of free sporozoites, and the number of sporocysts containing unhatched sporozoites, were determined in an experimental mixture which did not contain any added Mab $E_2E_5$ (control) and in an experimental mixture which contained added Mab $E_2E_5$.

In order to investigate the importance of EtOS22 during excystation, parallel excystation assays were performed with and without the added presence of the $E_2E_5$ MAb. The number of hatched sporozoites and of sporocysts containing unhatched sporozoites was then determined in both assays (in each case 2 ml), and these data were compared with each other. The number of hatched sporozoites was $9.6 \times 10^6$ and $4.8 \times 10^6$ in the control and in the presence of the MAb, respectively. On the other hand, the number of sporocysts containing unhatched sporozoites increased from $2.0 \times 10^5$ to $2.2 \times 10^6$ (FIG. 6). The fact that the free sporozoites were reduced by about half while at the same time sporocysts containing unhatched sporozoites increased about 10-fold shows that modulating the activity of EtOS22 leads to inhibition of *Eimeria tenella* excystation and, consequently, modulating the activity of EtOS22 may be suitable for treating *Eimeria* infections.

Example 24

Testing Affinity-isolated Substances Against *Eimeria tenella* in Cell Culture

The in-vitro testing is effected on primary kidney cell cultures. For this, kidney tissue from 12-day-old laying-type chicks is dissected out aseptically and the kidney cells which are isolated from it are grown for monolayer tissue cultures in 96-well plates. The nutrient medium used is DMEM+5% fetal calf serum+2% glutamine+2% nonessential amino acids+1% HEPES+1% sodium pyruvate. After having been incubated for two days at 42° C. and 5% $CO_2$, the tissue cultures. are infected with excysted *Eimeria tenella* sporozoites. Proceeding from a stock solution concentration of 20 mg/ml in DMSO, affinity-isolated substances are diluted with nutrient medium down to a final concentration of 10 ppm and added to the infected cell cultures. On the 5$^{th}$ day after the infection, the cultures are assessed microscopically and the condition of the host cells, and also the number of intact schizonts and free merozoites (120 hours after infection) are determined. The activity is assessed as follows:

| Index | Assessment | Optical perception |
|---|---|---|
| 2 | Fully active | No intact parasites/well |
| 1 | Weakly active | 1-6 intact parasites/well |
| 0 | Inactive | Parasite number as in the infected control |
| T | Cytotoxic | Host cells have died (have become rounded) |

REFERENCES

Altschul, S. F., Gish, W., Miller, W., Myers, E. W., Lipman, D. J. (1990): Basic local alignment search tool. J. Mol. Biol. 215: 403-410.

Blin, N., Stafford, D. W. (1976): A general method for isolation of high molecular weight DNA from eukaryotes. Nucleic Acids Res. 3: 2303-2308.

Chomczynski, P. (1992): One-hour downward alkaline capillary transfer for blotting of DNA and RNA. Anal. Biochem. 201: 134-139

Feinberg, A. P., Vogelstein, B. (1984): "A technique for radiolabeling DNA restriction endonuclease fragments to high specific activity". Addendum. Anal. Biochem. 137:266-267.

Jacobsson, K., Frykberg, L. (1998): Gene VIII-based, phagedisplay vectors for selection against complex mixtures of ligands. Biotechniques 24:294-301.

Kyhse-Andersen, J. (1984): Electroblotting of multiple gels: a simple apparatus without buffer tank for rapid transfer of proteins from polyacrylamide to nitrocellulose. J. Biochem. Biophys. Methods 10:203-209.

Laemmli, U. K. (1970): Cleavage of structural proteins during the assembly of the head of bacteriophage T4. Nature 227:680-685.

Lihme, A., Schafer-Nielsen, C., Larsen, K. P., Muller, K. G., Bog-Hansen, T. C. (1986): Divinylsulphone-activated agarose. Formation of stable and non-leaking affinity matrices by immobilization of immunoglobulins and other proteins. J. Chromatogr. 376:299-305.

Morgenstern, B., Frech, K., Dress, A., Werner, T. (1998): DIALIGN: finding local similarities by multiple sequence alignment. Bioinformatics. 14:290-294.

Morgenstern, B. (1999): DIALIGN 2: improvement of the segment-to-segment approach to multiple sequence alignment. Bioinformatics. 15:211-218.

Mouafo, A. N., Weck-Heimann, A., Dubremetz, J. F., Entzeroth, R. (2002): Monoclonal antibodies specific for the two types of wall-forming bodies of *Eimeria tenella* macrogametes (Coccidia, Apicomplexa). Parasitol. Res. 88:217-224.

Muller, P. Y., Studer, E., Miserez, A. R. (2001): Molecular Biocomputing Suite: a word processor add-in for the analysis and manipulation of nucleic acid and protein sequence data. Biotechniques 31:1306, 1308, 1310-1306, 1308, 1313.

Nielsen, H., Engelbrecht, J., Brunak, S., von Heijne, G. (1997): A neural network method for identification of prokaryotic and eukaryotic signal peptides and prediction of their cleavage sites. Int. J. Neural Syst. 8:581-599.

Roswell, D. F., White, E. H. (1978): The chemiluminescence of luminol and related hydrazides. Methods Enzymol. 57:409423.

Sambrook, J., Fritsch, E. F., Maniatis T., (1989) Molecular cloning. A laboratory manual. New York, Cold Spring Harbor Laboratory.

Sanger, F., Nickden, S., Coulson, A. R. (1977): DNA sequencing with chain-terminating inhibitors. Proc. Natl. Acad. Sci. U. S. A 74:5463-5467.

Tatusova, T. A., Madden, T. L. (1999): BLAST 2 Sequences, a new tool for comparing protein and nucleotide sequences. FEMS Microbiol. Lett. 174:247-250.

Thompson, J. D., Higgins, D. G., Gibson, T. J. (1994): CLUSTAL W: improving the sensitivity of progressive multiple sequence alignment through sequence weighting, position-specific gap penalties and weight matrix choice. Nucleic Acids Res. 22:4673-4680.

Zhang, L., Jacobsson, K., Strom, K., Lindberg, M., Frykberg, L. (1999): Staphylococcus aureus expresses a cell surface protein that binds both IgG and beta2-glycoprotein I. Microbiology 145 (Pt 1):177-183.

Bhogal, B. S. et al. (1992): Potential of a recombinant antigen as a prophylactic vaccine for day-old broiler chickens against *Eimeria tenella* infections. Vet. Immunol. Immunopathol. 31:323-335.

Binger, M. H., Hug D., Weber, G., Schikdknecht, E., Humbelin M., Pasamontes L. (1993): Cloning and, characterization of a surface antigen of *Eimeria tenella* merozoites and expression using a recombinant vaccinia virus. Mol. Biochem. Parasitol. 61:179-188.

Brake, D. A. (2002): Vaccinology for control of apicomplexan parasites: a simplified language of immune programming and its use in vaccine design. Int. J. Parasitol. 32:509-515

Chapman, H. D., Cherry, T. E., Danforth, H. D., Richards G., Shirley, M. W., Williams, R. B. (2002): Sustainable coccidiosis control in poultry production: the role of live vaccines. Int. J. Parasitol. 32:617-629.

Clarke, L. E, Messer, L. I., Wisher, M. H. (1986): Antigens of *Eimeria* cloned and expressed in *E. coli*. J. Cell Biochem. 10:A 145.

Coombs, G. H., Müller, S. (2002): Recent advances in the search for new anti-coccidial drugs. Int. J. Parasitol 32:497-508.

Crane, M. S. J. et al. (1991): Cross-protection against four species of chicken coccidia with a single recombinant antigen. Infect. Immun. 59:1271-1277.

Danforth, H. D., Augustine, P. C. (1985): Use of hybridoma antibodies and recombinant DNA technology in protozoan vaccine development. Avian Diseases 30:37-42.

Eschenbacher, K. H., Eggli, P., Wallach, M., Braun, R. (1996): Characterisation of a 14 kda oocyst wall protein of *Eimeria tenella* and *Eimeria acervulina*. Parasitol 112(2): 169-176.

Files, J. G., Paul, L. S., Gabe, J. D. (1987): Identification and characterization of the gene for a major surface antigen of *Eimeria tenella*. In: Molecular strategies of parasite invasion. N. Agabian, H. Goodman and N. Noguiera (eds.). UCLA Symp. Mol. Cell. Biol., New Series, Vol. 32. Alan R. Liss, Inc., New York pp 713-723

Greif, G., Harder, A., Haberkorn, A. (2001): Chemotherapeutic approaches to protozoa: Coccidiae—current level of knowledge and outlook. Parasitol Res 87:973-975

Jenkins, M. C. (1998): Progress on developing a recombinant coccidiosis vaccine. Int. L. Parasitol. 28:1111-9

Ko, C., Smith, C. K. II, McDonell, M. (1990): Identification and characterization of a target antigen of a monoclonal antibody directed against *Eimeria tenella* merozoites. Mol. Biochem. Parasitol. 41:53-64

Levine, L. D. et al. (1980): A newly revised classification of Protozoa. J. Protozool. 27:37-58.

Miller, G. A. et al. (1989): Characterization and vaccine potential of a novel recombinant coccidial antigen. Infect. Immun. 57:2014-2020.

Pogonka, T., Klotz, C., Kovacs, F., Lucius, R. (2003): A single dose of recombinant *Salmonella typhimurium* induces specific humoral immune responses against heterologous *Eimeria tenella* antigens in chicken. Int. J. Parasitol. 33:81-88

Rose, M. E., Wakelin, D. (1990): Immunity to coccidiosis. In: Coccidiosis of man and domestic animals, Long, P. L. (ed.), CRC Press, pp. 281-306.

Sangster, N., Batterham, P., Chapman, H. D., Duraisingh, M., Jambre, L. L., Shirley, M., Upcroft, J., Upcroft, P. (2002):

Resistance to antiparasitic drugs: the role of molecular diagnosis. Int. J. Parasitol. 32:637-653

Silva, A., Kawazoe, U., Freitas, F. F. T., Gatti, M. S. V., Dolder, H., Schumacher, R. I., Juliano, M. A., Silva, M. J., Leite, A. (2002): Avian anticoccidial activity of a novel membrane-interactive peptide selected from phage display libraries. Molec. Biochem. Parasitol. 120:53-60.

Stiff, M., Bafundo, K. W. (1993): Development of immunity in broilers continuously exposed to Eimeria sp. Avian Diseases 37:295-301.

Vermeulen, A. N. (1998): Progress in recombinant vaccine development against coccidiosis. A review and prospects into the next millenium. Int. J. Parasitol. 28:1121-1130.

Vermeulen, A. N., Schaap, D. C., Schetters, P. M. (2001): Control of coccidiosis in chickens by vaccination. Vet. Parasitol. 100:13-20.

Wallach, M., Halabi, A., Pillemer, G., Sar-Shalom, O., Mencher, D., Gilad, M., Bendheim, U., Danforth, H. D., Augustine, P. C. (1992): Maternal immunization with gametocyte antigens as a means of providing protective immunity against Eimeria maxima in chickens. Infection and Immunity 60:2036-2039.

Williams, R. B. (2002): Anticoccidial vaccines for broiler chickens: pathway to success. Avian Pathology 31:317-353.

Wan, K-L., Chong, S-P., Ng, S-T., Shirley, M. W., Tomley, F. M., Jangi, M. S. (1999): A survey of genes in Eimeria tenella merozoites by EST sequencing. Int. J. Parasitol 29:1885-1892.

Comes, A. M., Humbert, J. F., Cabaret, J., Elard, L. (1996): Using molecular tools for diagnosis in veterinary parasitology. Vet. Res. 27 (4-5):333-42

Ellis, J. & Bumstead, J. (1990): Eimeria species: studies using rRNA and rDNA probes. Parasitology 101:1-6.

Gasser, R. B., Woods, W. G., Wood, J. M., Ashdown, L., Richards, G., Whithear, K. G. (2001): Automated, fluorescence-based approach for the specific diagnosis of chicken coccidiosis. Electrophoresis 22 (16):3546-50

Johnston, D. A., Fernando, M. A. (1997): Isoenzymes of eimeria from the domestic fowl: electrophoretic variants among species, strains and clones. Parasitol. Res. 83(5): 464-70

Long, P. L., and Reid, W. M. (1982): A guide to the diagnosis of coccidiosis in chickens, Research Report 404, University of Georgia, Athens.

Molloy, J. B., Eaves, F. W., Jeston, P. J., Minchin, C. M., Stewart, N. P., Lew, A. E., Jorgensen, W. K. (1998): Detection of Eimeria acervulina using the polymerase chain reaction. Avian Dis. 42(1):119-23.

Procunier, J. D., Fernando, M. A., Barta, J. R. (1993): Species and strain differentiation of Eimeria spp. Of the domestic fowl using DNA polymorphisms amplified by arbitrary primers. Parasitol. Res. 79:98-102

Schnitzler, B. E., Thebo, P. L., Mattson, J. G., Tomley, F. M., Shirley, M. W.; (1998): Development of a diagnostic PCR assay for the detection and discrimination of four pathogenic Eimeria species of the chicken. Avian Pathology 27:490-497.

Sambrook, J. and Russell, D. W., (2001): Molecular Cloning. A Laboratory Manual. Cold Spring Harbor Laboratory Press. New York.

The invention claimed is:

1. An isolated polynucleotide consisting of:
   a) the sequence of SEQ ID NO: 1; or
   b) a polynucleotide which differs from a polynucleotide having the sequence of SEQ ID NO: 1 due to the degeneracy of the genetic code.

2. A vector or expression system which contains at least one of the polynucleotides as claimed in claim 1.

3. A host cell which harbors the vector or the expression system as claimed in claim 2.

4. A method for preparing a polypeptide having SEQ ID NO: 2 using the host cell as claimed in claim 3.

5. A method for detecting a polynucleotide as claimed in claim 1, wherein a polynucleotide as claimed in claim 1 is hybridized with the nucleic acid material from a biological sample and the hybridization is detected.

6. The method as claimed in claim 5, wherein the hybridization is detected using the polymerase chain reaction.

* * * * *

SEQUENCE LISTING

```
<160> NUMBER OF SEQ ID NOS: 24

<210> SEQ ID NO 1
<211> LENGTH: 1186
<212> TYPE: DNA
<213> ORGANISM: Eimeria tenella
<220> FEATURE:
<221> NAME/KEY: CDS
<222> LOCATION: (83)..(679)

<400> SEQUENCE: 1
caggacccca aaataaaatc aaaggctatc acactatttt acttcttaac cgtttactga      60
ggctacaaga acaagtttga ag atg agg act atc cta gcc acc cta gtc ggt     112
                         Met Arg Thr Ile Leu Ala Thr Leu Val Gly
                           1               5                  10 ttc aca gcc tgc gca gcc gtt gct gca gac gga gca cct gag tat cct     160
Phe Thr Ala Cys Ala Ala Val Ala Ala Asp Gly Ala Pro Glu Tyr Pro
                 15                  20                  25 tct cag ctt gca gtt gaa atc gat cca gaa gcg att att gcg atc cag     208
Ser Gln Leu Ala Val Glu Ile Asp Pro Glu Ala Ile Ile Ala Ile Gln
             30                  35                  40 caa gat gca aac gcc gac cca cgt ctc ttt ttc cca ctg agc ggg ctt     256
Gln Asp Ala Asn Ala Asp Pro Arg Leu Phe Phe Pro Leu Ser Gly Leu
         45                  50                  55 gtc tcc gcc aaa ctt gcc aaa gtc ttt caa ccc aac ata tac cca acc     304
Val Ser Ala Lys Leu Ala Lys Val Phe Gln Pro Asn Ile Tyr Pro Thr
     60                  65                  70 cct cct agt ccc cag aca act tac cac ttt cac ctc cat cct cat ccc     352
```

```
Pro Pro Ser Pro Gln Thr Thr Tyr His Phe His Leu His Pro His Pro
 75                  80                  85                  90 cat tat ccg cat cct cag cca agt tat cct cat cct caa ccc cat cat    400
His Tyr Pro His Pro Gln Pro Ser Tyr Pro His Pro Gln Pro His His
             95                 100                 105 cct cat cct cat cct tat cat cct cat cct cat ccc cat cat cct cat    448
Pro His Pro His Pro Tyr His Pro His Pro His Pro His His Pro His
            110                 115                 120 cct cat ccc cat caa cat cct cat cgt cat ccc gac cat cat ccc cac    496
Pro His Pro His Gln His Pro His Arg His Pro Asp His His Pro His
        125                 130                 135 cat cat cct cac cat cat cat cat gaa cat aat gtt cat gtg cct caa    544
His His Pro His His His His His Glu His Asn Val His Val Pro Gln
    140                 145                 150 cat cag cac gct caa cac aac ggc cac cag aac aac ggt ggc cca gct    592
His Gln His Ala Gln His Asn Gly His Gln Asn Asn Gly Gly Pro Ala
155                 160                 165                 170 cat tat cac cat gac tac cat ttt gcg cat cct cat caa gag aac cag    640
His Tyr His His Asp Tyr His Phe Ala His Pro His Gln Glu Asn Gln
                175                 180                 185 cat cac cgc gag gaa gag cag ctt acc gac atc aac taa gctattggtc     689
His His Arg Glu Glu Glu Gln Leu Thr Asp Ile Asn
            190                 195 gggaattaag gtgcttagtc tcagtagtca gtacagtact aggctacgtc tgagatcttc  749
atggcaaaga ggtaccagcc accaagctga ctcggctatg ttttattaga caaatttaaa  809 tttaagggt cccagtttca gtctctgcag gtctgcccct gaaagcacga gaggggccta   869
aagggtgatt ggagctgcaa atacagctgc aaatgcagct gcaaagtgcc gcttcaaaaa  929
agggacaggc ttcccgccaa aattttggga tcatacctat caatgcttcg agaaaacata  989
gaaaacaaaa gcactgaaga acgttcatag tcggtagttt taggggcatg ccgtgtgcta  1049
aaatcccatc gaaccttcag gtacacctga tcgttacgaa gtacacacca ccggtcactc  1109
tcaacgcgca ccactagagc gagagctgct tcagggatgc agcgagatgt cgactcagag  1169
gtcctacatt aaaggga                                                1186

<210> SEQ ID NO 2
<211> LENGTH: 198
<212> TYPE: PRT
<213> ORGANISM: Eimeria tenella

<400> SEQUENCE: 2

Met Arg Thr Ile Leu Ala Thr Leu Val Gly Phe Thr Ala Cys Ala Ala
1               5                   10                  15

Val Ala Ala Asp Gly Ala Pro Glu Tyr Pro Ser Gln Leu Ala Val Glu
            20                  25                  30

Ile Asp Pro Glu Ala Ile Ile Ala Ile Gln Gln Asp Ala Asn Ala Asp
        35                  40                  45

Pro Arg Leu Phe Phe Pro Leu Ser Gly Leu Val Ser Ala Lys Leu Ala
    50                  55                  60

Lys Val Phe Gln Pro Asn Ile Tyr Pro Thr Pro Ser Pro Gln Thr
65                  70                  75                  80

Thr Tyr His Phe His Leu His Pro His Pro Tyr Pro His Pro Gln
                85                  90                  95

Pro Ser Tyr Pro His Pro Gln Pro His His Pro His Pro Tyr
            100                 105                 110

His Pro His Pro His Pro His His Pro His Pro His Pro His Gln His
```

-continued

```
              115                 120                 125
Pro His Arg His Pro Asp His His Pro His His Pro His His
    130                 135                 140

His His Glu His Asn Val His Val Pro Gln His Gln His Ala Gln His
145                 150                 155                 160

Asn Gly His Gln Asn Asn Gly Gly Pro Ala His Tyr His His Asp Tyr
                165                 170                 175

His Phe Ala His Pro His Gln Glu Asn Gln His Arg Glu Glu Glu
            180                 185                 190

Gln Leu Thr Asp Ile Asn
        195

<210> SEQ ID NO 3
<211> LENGTH: 597
<212> TYPE: DNA
<213> ORGANISM: Eimeria tenella

<400> SEQUENCE: 3
atgaggacta tcctagccac cctagtcggt ttcacagcct gcgcagccgt tgctgcagac     60
ggagcacctg agtatccttc tcagcttgca gttgaaatcg atccagaagc gattattgcg    120
atccagcaag atgcaaacgc cgacccacgt ctctttttcc cactgagcgg gcttgtctcc    180
gccaaacttg ccaaagtctt tcaacccaac atatacccaa cccctcctag tccccagaca    240
acttaccact tcacctcca tcctcatccc cattatccgc atcctcagcc aagttatcct     300
catcctcaac cccatcatcc tcatcctcat ccttatcatc ctcatcctca tccccatcat    360
cctcatcctc atcccatca acatcctcat cgtcatcccg accatcatcc ccaccatcat    420
cctcaccatc atcatcatga acataatgtt catgtgcctc aacatcagca cgctcaacac    480
aacggccacc agaacaacgg tggcccagct cattatcacc atgactacca ttttgcgcat    540
cctcatcaag agaaccagca tcaccgcgag gaagagcagc ttaccgacat caactaa      597

<210> SEQ ID NO 4
<211> LENGTH: 25
<212> TYPE: DNA
<213> ORGANISM: Artificial Sequence
<220> FEATURE:
<223> OTHER INFORMATION: Primer A17-22-up

<400> SEQUENCE: 4
tcctcatcct tatcatcctc atcct                                             25

<210> SEQ ID NO 5
<211> LENGTH: 18
<212> TYPE: DNA
<213> ORGANISM: Artificial Sequence
<220> FEATURE:
<223> OTHER INFORMATION: Primer A17-112-lo

<400> SEQUENCE: 5
gtggggatga tggtcggg                                                     18

<210> SEQ ID NO 6
<211> LENGTH: 33
<212> TYPE: DNA
<213> ORGANISM: Artificial Sequence
<220> FEATURE:
<223> OTHER INFORMATION: Primer A17-f-length-64-up

<400> SEQUENCE: 6
```

-continued caggacccca aaataaaatc aaaggctatc aca    33

<210> SEQ ID NO 7
<211> LENGTH: 25
<212> TYPE: DNA
<213> ORGANISM: Artificial Sequence
<220> FEATURE:
<223> OTHER INFORMATION: Primer A17-f-length-1176-lo

<400> SEQUENCE: 7
tgaccggtgg tgtgtacttc gtaac    25

<210> SEQ ID NO 8
<211> LENGTH: 25
<212> TYPE: DNA
<213> ORGANISM: Artificial Sequence
<220> FEATURE:
<223> OTHER INFORMATION: Primer EtACTIN-up

<400> SEQUENCE: 8
ctgtgagaag aaccgggtgc tcttc    25

<210> SEQ ID NO 9
<211> LENGTH: 24
<212> TYPE: DNA
<213> ORGANISM: Artificial Sequence
<220> FEATURE:
<223> OTHER INFORMATION: Primer EtACTIN-lo

<400> SEQUENCE: 9
cgtgcgaaaa tgccggacga agag    24

<210> SEQ ID NO 10
<211> LENGTH: 32
<212> TYPE: DNA
<213> ORGANISM: Artificial Sequence
<220> FEATURE:
<223> OTHER INFORMATION: Primer A17-max-90-up

<400> SEQUENCE: 10
tgaggactat cctagccacc ctagtcggtt tc    32

<210> SEQ ID NO 11
<211> LENGTH: 32
<212> TYPE: DNA
<213> ORGANISM: Artificial Sequence
<220> FEATURE:
<223> OTHER INFORMATION: Primer A17-max-150-up

<400> SEQUENCE: 11
gagcacctga gtatccttct cagcttgcag tt    32

<210> SEQ ID NO 12
<211> LENGTH: 32
<212> TYPE: DNA
<213> ORGANISM: Artificial Sequence
<220> FEATURE:
<223> OTHER INFORMATION: Primer A17-max-533-lo

<400> SEQUENCE: 12
tatgttcatg atgatgatgg tgaggatgat gg    32

<210> SEQ ID NO 13
<211> LENGTH: 32
<212> TYPE: DNA
<213> ORGANISM: Artificial Sequence

```
<220> FEATURE:
<223> OTHER INFORMATION: Primer A17-max-631-lo

<400> SEQUENCE: 13
aggatgcgca aaatggtagt catggtgata at                              32

<210> SEQ ID NO 14
<211> LENGTH: 27
<212> TYPE: DNA
<213> ORGANISM: Artificial Sequence
<220> FEATURE:
<223> OTHER INFORMATION: Primer pG8SAET-up

<400> SEQUENCE: 14
taggtgtagg tattgcatct gtaactt                                    27

<210> SEQ ID NO 15
<211> LENGTH: 27
<212> TYPE: DNA
<213> ORGANISM: Artificial Sequence
<220> FEATURE:
<223> OTHER INFORMATION: Primer pG8SAET-lo

<400> SEQUENCE: 15
cgatatattc ggtcgctgag gcttgca                                    27

<210> SEQ ID NO 16
<211> LENGTH: 27
<212> TYPE: DNA
<213> ORGANISM: Artificial Sequence
<220> FEATURE:
<223> OTHER INFORMATION: Primer pG8SAET-seq-up-140

<400> SEQUENCE: 16
atgatgactt tacaaataca tacaggg                                    27

<210> SEQ ID NO 17
<211> LENGTH: 32
<212> TYPE: DNA
<213> ORGANISM: Artificial Sequence
<220> FEATURE:
<223> OTHER INFORMATION: Primer A17-sequint-27-up

<400> SEQUENCE: 17
cgaggaagag cagcttaccg acatcaacta ag                              32

<210> SEQ ID NO 18
<211> LENGTH: 32
<212> TYPE: DNA
<213> ORGANISM: Artificial Sequence
<220> FEATURE:
<223> OTHER INFORMATION: Primer A17-sequint-44-up

<400> SEQUENCE: 18
ccgacatcaa ctaagctatt ggtcgggaat ta                              32

<210> SEQ ID NO 19
<211> LENGTH: 32
<212> TYPE: DNA
<213> ORGANISM: Artificial Sequence
<220> FEATURE:
<223> OTHER INFORMATION: Primer A17-sequint-385-lo

<400> SEQUENCE: 19
atgaggataa tttggctgag gatgcggata at                              32
```

```
<210> SEQ ID NO 20
<211> LENGTH: 32
<212> TYPE: DNA
<213> ORGANISM: Artificial Sequence
<220> FEATURE:
<223> OTHER INFORMATION: Primer A17-sequint-351-lo

<400> SEQUENCE: 20
ggatgaggat ggaggtgaaa gtggtaagtt gt                                   32

<210> SEQ ID NO 21
<211> LENGTH: 17
<212> TYPE: DNA
<213> ORGANISM: Artificial Sequence
<220> FEATURE:
<223> OTHER INFORMATION: Primer M13 reverse

<400> SEQUENCE: 21
cgagaaacag ctatgac                                                   17

<210> SEQ ID NO 22
<211> LENGTH: 16
<212> TYPE: DNA
<213> ORGANISM: Artificial Sequence
<220> FEATURE:
<223> OTHER INFORMATION: Primer M13 forward

<400> SEQUENCE: 22
gtaaaacgac ggccag                                                    16

<210> SEQ ID NO 23
<211> LENGTH: 20
<212> TYPE: DNA
<213> ORGANISM: Artificial Sequence
<220> FEATURE:
<223> OTHER INFORMATION: Primer T7-Promotor

<400> SEQUENCE: 23
attatgctga gtgatatccc                                                20

<210> SEQ ID NO 24
<211> LENGTH: 18
<212> TYPE: DNA
<213> ORGANISM: Artificial Sequence
<220> FEATURE:
<223> OTHER INFORMATION: Primer BGH reverse

<400> SEQUENCE: 24
tagaaggcac agtcgagg                                                  18
```